United States Patent [19]

Moll et al.

[11] Patent Number: 5,575,759
[45] Date of Patent: Nov. 19, 1996

[54] METHODS OF USING INFLATABLE RETRACTION DEVICES IN LAPAROSCOPIC SURGERY

[75] Inventors: Frederic H. Moll, San Francisco; Daniel T. Wallace, Mountain View; Jeffrey A. Smith, Sunnyvale; David C. Forster, Woodside; Albert K. Chin, Palo Alto, all of Calif.

[73] Assignee: Origin Medsystems, Inc., Menlo Park, Calif.

[21] Appl. No.: 457,396

[22] Filed: Jun. 1, 1995

Related U.S. Application Data

[60] Division of Ser. No. 134,573, Oct. 8, 1993, Pat. No. 5,425,357, which is a continuation-in-part of Ser. No. 794,590, Nov. 19, 1991, Pat. No. 5,309,896, which is a continuation-in-part of Ser. No. 706,781, May 29, 1991, abandoned.

[51] Int. Cl.$^6$ ............................................. A61B 17/02
[52] U.S. Cl. ................................... 600/207; 606/192
[58] Field of Search ................................ 600/207, 204; 606/192; 128/898

[56]     References Cited

U.S. PATENT DOCUMENTS

| 2,663,020 | 12/1953 | Cushman . | |
|---|---|---|---|
| 3,173,418 | 3/1965 | Baran | 128/351 |
| 3,626,949 | 12/1971 | Shute . | |
| 3,774,596 | 11/1973 | Cook | 128/5 |
| 3,831,587 | 8/1927 | Boyd | 128/6 |
| 3,863,639 | 2/1975 | Kleaveland | 128/303 |
| 3,882,852 | 5/1975 | Sinnreich | 128/276 |
| 3,961,632 | 6/1976 | Moossun | 127/347 |
| 4,077,412 | 3/1978 | Moossun | 128/347 |
| 4,083,369 | 4/1978 | Sinnreich | 128/276 |
| 4,137,906 | 2/1979 | Akiyama et al. | 128/2 |
| 4,240,433 | 12/1980 | Bordow | 128/276 |
| 4,271,839 | 6/1981 | Fogarty et al. | 128/344 |
| 4,291,687 | 9/1981 | Sinnreich | 128/129 |

(List continued on next page.)

FOREIGN PATENT DOCUMENTS

| 0010650 | 5/1980 | European Pat. Off. | A61M 31/00 |
|---|---|---|---|
| 0526721 | 6/1992 | European Pat. Off. | A61B 1/32 |
| 2847633 | 5/1979 | Germany | A61B 17/22 E2 |
| 797668 | 1/1981 | U.S.S.R. | A61B 17/2 |
| 1367947 | 3/1985 | U.S.S.R. | A61B 17/02 |
| 2071502 | 9/1981 | United Kingdom | A61B 17/02 |
| WO93/11824 | 12/1992 | WIPO | A61M 29/00 |

OTHER PUBLICATIONS

A. I. Gilbert, MD, FACS, "Sutureless Repair of Inguinal Hernia," 163 Am. J. Surgery, pp. 331–335 (1992, Mar.).
A. Guiarnieri, MD, et al., "A New Technique for Indirect Hernia Repair," 164 Am. J. Surgery, pp. 70–73 (1992 Jul.).
J. C. Hulbert, MD, et al., "Laparoscopic Retroperitoneal Lymphadenectomy: New Approach to Pathologic Staging of Clinical Stage I Germ Cell Tumors of the Testis," 6 J. Endourology, pp. 123–125, (1992, No. 2).
H. Ruckle, MD, et al., "Laparoscopic Pelvic Lymph Node Dissection: Assessment Intraoperative and Early Postoperative Complications," J. Endourology pp. 117–119, (1992, No. 2).

(List continued on next page.)

*Primary Examiner*—Michael H. Thaler
*Attorney, Agent, or Firm*—Limbach & Limbach L.L.P.

[57]     ABSTRACT

Apparatus for retracting an organ to gain access to treat a tissue. The apparatus has a main envelope, a second envelope, a first inflation device and a second inflation device. The main envelope encloses a main chamber, and includes a window and a removable window. The second envelope covers substantially all the main envelope, except the window and the removable window. The second envelope and the main envelope enclose a second chamber outside the main chamber. The first inflation device passes a fluid into the main chamber to expand the main chamber and the second chamber from a compacted state to retract the organ. The second inflation device passes a fluid into the second chamber to further expand the second chamber to maintain the organ in its retracted state after fluid has been released from the main chamber.

16 Claims, 18 Drawing Sheets

U.S. PATENT DOCUMENTS

| | | | |
|---|---|---|---|
| 4,430,076 | 2/1984 | Harris | 604/94 |
| 4,447,227 | 5/1984 | Kotsanis | 604/101 |
| 4,493,711 | 1/1985 | Chin et al. | 604/271 |
| 4,739,762 | 4/1988 | Palmaz | 128/343 |
| 4,775,371 | 10/1988 | Mueller, Jr. | 604/280 |
| 4,779,611 | 10/1988 | Grooters, et al. | 128/4 |
| 4,863,440 | 9/1989 | Chin | 604/271 |
| 4,878,495 | 11/1989 | Grayzel | 128/344 |
| 4,919,152 | 4/1990 | Ger | 128/898 |
| 4,944,443 | 7/1990 | Oddsen et al. | 227/19 |
| 4,966,583 | 10/1990 | Debbas | 604/98 |
| 4,984,564 | 1/1991 | Yuen | 128/20 |
| 5,002,557 | 3/1991 | Hasson | 606/191 |
| 5,007,898 | 4/1991 | Rosenbluth et al. | 604/54 |
| 5,049,132 | 9/1991 | Shaffer et al. | 604/101 |
| 5,083,576 | 1/1992 | Ruiz-Razura et al. | 128/898 |
| 5,084,061 | 1/1992 | Gau et al. | 606/192 X |
| 5,122,122 | 6/1992 | Allgood | 604/174 |
| 5,122,155 | 6/1992 | Eberbach | 606/213 |
| 5,141,515 | 8/1992 | Eberbach | 606/151 |
| 5,163,949 | 11/1992 | Bonutti | 606/192 |
| 5,176,692 | 1/1993 | Wilk et al. | 606/151 |
| 5,183,463 | 2/1993 | Debbas | 604/98 |
| 5,183,464 | 2/1993 | Dubrul et al. | 604/96 |
| 5,197,948 | 3/1993 | Ghodsian | 604/30 |
| 5,342,385 | 8/1994 | Norelli et al. | 606/193 |
| 5,345,927 | 9/1994 | Bonutti | 128/20 |

OTHER PUBLICATIONS

"Texas Team Routinely Performs Lymphadenectomy for Prostate Cancer Patients," Gen. Sug. News, p. 4, (1992, Feb.).

"For Selected Prostate Cancer Patients, Laparoscopicy Lymphadenectomy is Preferable to Open Surgery," Gen. Surg. News, p. 4, (1992, Feb.).

G. Ferzli, MD, FACS, et al., "Extraperitoneal Endoscopic Pelvic Lymph Node Dissection v. Lapaoscopic Lymph Node Dissection in the Staging of Prostatic & Bladder Carcinoma", 2 J. Laparoendoscopic Surg. pp. 219–222 (1992, No. 2).

H. M. Delany, MD, et al., "Extent of Peritoneal Adhesions & Local Tissue Reaction in Response to Absorable vs. Nonabsorbable Mesh," 40 Contemporary Surgery, pp. 29–36 (1992 PRIL).

A. Shafik, MD, "Extraperitoneal Laparoscopic Lymphadenectomy in Prostatic Cancer: Preliminary Report of a New Approach," 6 J. Endourology, pp. 113–116 (1992, No. 2).

"Four Surgeons Describe Their Separate Techniques for Performing Laparoscopic Inguinal Hernia Repair", Laparoscopy News, Oct. 1991.

C. R. Nezhat, MD, et al., "Laparoscopic Radical Hysterectomy with Paraaortic and Pelvic Node Dissection," 166 Am. J. Obstet. Gynecol., pp. 864–865 (1992, No. 3). Laparoscopy in Focus, pp. 5–7, (1991, No. 1).

M. E. Arregui, MD, et al., "Laparoscopic Mesh Repair of Inguinal Hernia Using a Properitoneal Approach: A Preliminary Report," 2 Surg. Laparoscopy & Endoscopy, pp. 53–58 (1992, No. 1).

C. J. Bellis, PhD, MD, "Immediate Return to Unrestricted Work after Inguinal Herniorrhaphy. Personal Experiences with 27,267 Cases, Local Anesthesia, and Mesh," 77 Int. Surg. pp. 167–169 (1992).

5,575,759

METHODS OF USING INFLATABLE RETRACTION DEVICES IN LAPAROSCOPIC SURGERY

This is a divisional of application Ser. No. 08/134,573, filed Oct. 8, 1993, now U.S. Pat. No. 5,425,357, which is a continuation-in-part of application Ser. No. 07/794,590, filed Nov. 19, 1991, now U.S. Pat. No. 5,309,896, which is a continuation-in-part of application Ser. No. 07/706,781, filed May 29, 1991, now abandoned.

FIELD OF THE INVENTION

This application relates to inflatable dissectional retraction devices for use in laparoscopic surgery, and surgical procedures using inflatable dissectional retraction devices.

BACKGROUND OF THE INVENTION

Laparoscopy dates back to the mm of the 20th Century. Early laparoscopic techniques were used primarily for diagnostic purposes to view the internal organs without the necessity of conventional surgery. Since the 1930s, laparoscopy has been used for sterilization and, more recently, for suturing of hemas. U.S. Pat. Nos. 4,919,152 and 4,944,443 are concerned with techniques for suturing hemas. Another recent innovation is the use of laparoscopic surgery for removing the gallbladder.

U.S. patent application Ser. No. 07/706,781, the application of which this application is a Continuation-in-Part and which is incorporated herein by reference, describes an apparatus and method wherein the abdominal wall is lifted away from the underlying abdominal organs by an inflatable device which is introduced laparoscopically and, once in place, inflated to engage and lift an extensive area of the abdominal wall.

Even when such lifting techniques are used, it is still necessary to retract other organs to gain access to the organ or tissue to be treated or observed. In other procedures, to gain access to the organ or tissue to be treated or observed, it is necessary to separate the organ to be treated from tissue surrounding it. For example, to be able to observe the outer surface the heart, the outer surface of the heart has to be separated from the pericardium. To obtain the necessary retraction, current laparoscopic procedures use several small retractors inserted though plural incisions. Because such retractors have a relatively small surface area, they tend to damage and/or cause trauma to the retracted organs or tissue. Moreover, the requirement for plural incisions to heal may delay the patient's recovery.

One of the inventors of the present invention has used a modified Foley catheter to retract organs and tissue with less damage. The modified Foley catheter comprises a small, substantially spherical balloon on the end of a catheter which is inserted through a small incision into the body. After insertion, the balloon is inflated. The modified Foley catheter is used in a similar manner to a conventional retractor, but the retracted organ or tissue is contacted by the relatively large surface area of the balloon. Such a retractor reduces damage to retracted organs or tissues, but is inconvenient to use because it has to be kept in place by means of an external clamping arrangement, and its relatively large inflated balloon tends to obstruct access to the site to be treated.

U.S. patent application Ser. No. 07/794,590, of which this application is a Continuation-in-Part (the "parent application") and which is also incorporated herein by reference, discloses a number of different inflatable retraction devices for retracting an organ or a tissue (an "organ") to provide access to an organ or a tissue (a "tissue"). The inflatable retraction devices disclosed in the parent application are multi-chambered. An inflatable retraction device is packaged in a collapsed and compacted state, and is laparoscopically placed adjacent to the organ to be retracted. The large, main chamber of the inflatable retraction device is then inflated to expand the main chamber, which retracts the organ. Expanding the inflatable retraction device not only retracts the organ, but also causes the expanded main chamber to obstruct access to the tissue.

Once the main chamber of the inflatable retraction device is fully expanded, a second inflatable chamber is inflated. The second chamber, although normally providing less of a retraction force than the main chamber, provides sufficient retraction force to maintain the organ in its retracted state after the inflation pressure in the main chamber is released. Then, apertures are cut in the envelope of the main chamber to provide access to the tissue to be treated. The tissue is treated using instruments passed through the main chamber.

Experience with performing a variety of different procedures using the inflatable retraction devices disclosed in the parent application has indicated a number of desirable performance improvements, including: increasing the retraction force exerted by the second chamber; increasing the resistance of the both inflatable chambers to accidental deflation; increasing the ease of expanding the main chamber from its collapsed and compacted state; reducing the bulk of the inflatable retraction device in its collapsed and compacted state; and eliminating the need to cut apertures in the envelope of the main chamber to provide access to treat the tissue. One aspect of the invention in the parent application involved cutting an aperture in the envelope of the main chamber using a sharp object near the organ retracted by the inflatable retraction device.

The parent application also describes using the two-chambered inflatable retraction device for properitoneal hernia repair. A hernia is the protrusion of part of a body part or structure through a defect in the wall of a surrounding structure. Most commonly, a hernia is the protrusion of part of abdominal contents, including bowel, through a tear or weakness in the abdominal wall, or through the inguinal canal into the scrotum.

An abdominal hernia is normally repaired by suturing or stapling a mesh patch over the site of the tear or weakness. The anatomical weakness of the hernia can be approached from inside or outside the abdomen. If approached intra-abdominally, the mesh patch, which has a rough surface, can irritate the bowel and cause adhesions. It is therefore preferred to install the patch properitoneally, in which the mesh patch is attached to the properitoneal fascia of the abdominal wall, and covered by the peritoneum. To attach the mesh patch to the properitoneal fascia, the peritoneum must be dissected from the properitoneal fascia.

The use of laparoscopic techniques to perform hernia repair is becoming increasingly common. In the conventional procedure for carrying out a hernia repair laparoscopically, an endoscope and instruments are introduced into the belly through one or more incisions in the abdominal wall, and are advanced through the belly to the site of the hernia. Then, working from inside the belly, a long incision is made in the peritoneum covering the site of the hernia. A small part of the pefitoneum is dissected from the properitoneal fat layer to provide access to the fat layer. This is conventionally done by blunt dissection. In this procedure, it is difficult to dissect the peritoneum cleanly since patchy layers of properitoneal fat tend to adhere to the peritoneum.

In an alternative known extraperitoneal laparoscopic hernia repair procedure, an incision is made in the abdominal wall close to the site of the hernia. The incision is made through the abdominal wall as far as the properitoneal fat layer. The peritoneum is then blunt dissected from the properitoneal fat layer by passing a finger or a rigid probe through the incision and sweeping the finger or rigid probe under the peritoneum. After the peritoneum is dissected from the properitoneal fat layer, the space between the peritoneum and the properitoneal fat layer is insufflated to provide a working space in which to apply the mesh patch to the properitoneal fascia. During the blunt dissection process, it is easy to puncture through the peritoneum, which can be quite thin. A puncture destroys the ability of the space between the peritoneum and the fascia to hold gas insufflation. Also, it is difficult to dissect the peritoneum cleanly since patchy layers of properitoneal fat tend to adhere to the peritoneum.

The laparoscopic hernia repair technique described in the parent application enables a mesh patch to be attached to the properitoneal fascia without breaching the peritoneum. An incision is made through the abdominal wall as far as the properitoneal fat layer. An inflatable retraction device of the type described above is pushed through the incision into contact with the peritoneum, and is used to nudge the peritoneum from the underlying layers. The main chamber of the inflatable retraction device is then inflated to expand the inflatable retraction device towards the site of the hernia. As it expands, the inflatable retraction device gently dissects the peritoneum from the underlying layers.

Once the main chamber of the inflatable retraction device is fully expanded, the second chamber is inflated. The second chamber enables the inflatable retraction device to continue to maintain separation of the peritoneum from the overlying layers after the inflation pressure in the main chamber has been released.

One or more apertures are then cut in the envelope of the main chamber to provide access to the site of the hernia for instruments passed into the main chamber. With such an arrangement, instruments pass to the site of the hernia through the main chamber situated between the peritoneum and the overlying layers. In this way, a mesh patch can be attached to the properitoneal fascia without breaching the peritoneum.

Experience with this hernia repair technique has shown that the desirable improvements to the inflatable retraction device set forth above are also desirable when the inflatable retraction device is used to perform hernia repair. In addition, a number of additional improvements specific to inflatable retraction devices used for hernia repair have been identified, including: using a single inflatable retraction device usable to treat both sides of a bilateral hernia; providing an ability for the surgeon to locate the inflatable retraction device relative to the site of the hernia by feel when inserting the inflatable retraction device prior to expansion; and enabling the packaged inflatable retraction device to perform blunt dissection without the need to inflate the main chamber.

U.S. patent application Ser. No. 07/911,714, which is also a Continuation-in-Part of the parent application, and which is also incorporated herein by reference, discloses a properitoneal hernia repair technique which differs from the technique using the above-described two-chambered inflatable retraction device. The technique described in the '714 application uses a single-chambered inflatable retraction device to create a working space at the site of the hernia. The inflatable retraction device is removed and the working space is insufflated prior to treating the hernia.

A small incision is made at the umbilicus through the abdominal wall as far as the peritoneum. The single-chambered inflatable retraction device is introduced through the incision and is used to nudge the peritoneum away from the adjacent fat layer. The chamber is then partially inflated to expand the chamber, which dissects more of the peritoneum away from the adjacent fat layer. The chamber is then deflated and advanced towards the site of the hernia. The inflating and advancing process can be repeated to form a tunnel between the incision and the site of the hernia.

When the site of the hernia is reached, the chamber is fully expanded to create a working space at the site of the hernia. An endoscope can be inserted into the expanded chamber to obtain a visual conformation of the hernia defect. The inflatable retraction device is then withdrawn from the working space, and a trocar tube anchored by a small balloon is inserted into the incision. Insufflation gas is passed through the trocar tube to insufflate the tunnel and the working space. The hernia is then treated using instruments passed into the insufflated working space through the insufflated tunnel.

Experience with using the single-chambered balloon technique just described has shown that the peritoneum can sometimes rise up and obstruct access to the site of the hernia. This occurs if the peritoneum is breached during the dissection process, and insufflation gas leaks into the abdominal cavity. This equalizes the pressure across the peritoneum, and the insufflation pressure no longer depresses the peritoneum away from the site of the hernia. It has also been found that blood accumulates in the tunnel leading to the site of the hernia, and contaminates the lens of the endoscope when the endoscope is passed through the tunnel. The endoscope must then be withdrawn from the tunnel, its lens cleaned, and another attempt to insert the endoscope made.

OBJECTS AND SUMMARY OF THE INVENTION

It is an object of the present invention to increase the retraction force exerted by the second chamber.

It is a further object of the invention to increase the resistance of the both inflatable chambers to accidental deflation.

It is a further object of the invention to increases the ease of expanding the main chamber from its collapsed and compacted state.

It is a further object of the invention to reduce the bulk of the inflatable retraction device in its collapsed and compacted state.

It is a further object of the invention to eliminate the need to cut apertures in the envelope of the main chamber to provide access to treat the tissue.

It is a further object of the invention to control the inflation pressure in the main chamber to prevent the pressure in the main chamber from rising when the second chamber is expanded.

It is a further object of the invention to reduce localized stress in the main envelope and the second envelope.

It is a further object of the invention to increase the ease and accuracy with which the inflatable retraction device can be positioned relative to the organ to be retracted.

It is a further object of the present invention to provide a single inflatable retraction device usable to treat both sides of a bilateral hernia.

It is a further object of the invention to provide an ability for the surgeon to locate the inflatable retraction device relative to the site of the hernia by feel when inserting the inflatable retraction device prior to expansion.

If is a final object of the invention to enable the packaged inflatable retraction device to perform blunt dissection without the need to inflate the main chamber.

Accordingly, the invention provides an apparatus for retracting an organ to gain access to treat a tissue. The apparatus comprises a main envelope, a second envelope, a first inflation device and a second inflation device. The main envelope encloses a main chamber, and includes a window and a removable window. The second envelope covers substantially all the main envelope, except the window and the removable window. The second envelope and the main envelope enclose a second chamber outside the main chamber. The first inflation device passes a fluid into the main chamber to expand the main chamber and the second chamber from a compacted state to retract the organ. The second inflation device passes a fluid into the second chamber to further expand the second chamber to maintain the organ in its retracted state after fluid has been released from the main chamber.

The invention also provides a pressure control valve that allows fluid to pass in a first direction, and allows fluid to pass in a second direction, opposite to the first direction, only when fluid has a pressure in the second direction exceeding a predetermined limit. The valve comprises a valve body including a valve seat. The valve also comprises a one-way valve seating on the valve seat in the valve body. The one-way valve is oriented to allow fluid to pass in the first direction, and to prevent fluid from passing in the second direction. Finally, the valve comprises a compression spring disposed between the one-way valve and the valve body to apply a seating force between the one-way valve and the valve seat.

The invention also provides a method for properitoneal hernia repair. In the method, an inflatable retraction device is provided in a compacted state. The inflatable retraction device includes a main envelope enclosing a main chamber and including a window and a removable window; and a second envelope covering substantially all the main envelope, except the window and the removable window. The second envelope and the main envelope enclose a second chamber outside the main chamber. The device also includes an attachment point centered in the removable window, and an insertion shaft passing through the main chamber, and having a distal end temporarily attached to the attachment point. The attachment point provides a distal tip for inflatable retraction device.

Further, in the method, an incision is made through the abdominal wall at the umbilicus as far as the properitoneal layer, and the distal tip of the inflatable retraction device is inserted into the incision. The inflatable retraction device is then used to dissect the peritoneum from the properitoneal layer while advancing the inflatable retraction device inferiority between the peritoneum and the properitoneal layer towards the hernia. A fluid is passed into the main chamber to expand the main chamber and the second chamber from the compacted state and to dissect the peritoneum from the properitoneal layer. A fluid is passed into the second chamber to further expand the second chamber. Fluid is then released from the main chamber, and the removable window is detached from the main envelope.

Finally, the invention provides a method for retracting an organ to gain access to treat a tissue. In the method, an inflatable retraction device is provided in a compacted state. The inflatable retraction device includes a main envelope enclosing a main chamber, and including a window and a removable window. The device also includes a second envelope covering substantially all the main envelope, except the window and the removable window. The second envelope and the main envelope enclose a second chamber outside the main chamber. The inflatable retraction device is placed in the compacted state adjacent the organ. A fluid is passed into the main chamber to expand the main chamber and the second chamber from the compacted state to retract the organ. A fluid is passed into the second chamber to further expand the second chamber. Fluid is released from the main chamber. And the removable window is detached from the main envelope.

BRIEF DESCRIPTION OF THE DRAWINGS

FIG. 10A shows the inflatable retraction device according to the invention prior to insertion;

FIG. 10B shows an initial displacement of the peritoneum by the inflatable retraction device;

FIG. 10C shows the inflatable retraction device according to the invention dissecting the peritoneum away from the properitoneal layer as the device is advanced towards the hernia;

FIG. 10D shows the surgeon locating the distal tip of the inflatable retraction device at the hernia by feel;

FIG. 10E shows the inflatable retraction device after the main chamber has been expanded to dissect more of the peritoneum from the properitoneal layer;

FIG. 10F shows the inflatable retraction device after the second chamber has been expanded;

FIG. 10G shows the inflatable retraction device after the insertion device has been removed;

FIG. 10H shows a trocar driven through abdominal wall and the top-wall window;

FIG. 10I shows the inflatable retraction device after the removable window has been removed;

FIG. 10J shows insufflation gas passing through the main chamber to insufflate the working space; and FIG. 10K shows mesh being stapled over the hernia using a laparoscopic stapler passed through the main chamber.

FIG. 11B shows the inflatable retraction device according to the invention prior to insertion;

FIG. 11C shows the inflatable retraction device according to the invention inserted into the abdominal cavity and positioned with the button in the center of the removable window adjacent the liver;

FIG. 11D shows the inflatable retraction device after the main chamber has been expanded to retract the liver;

FIG. 11E shows the inflatable retraction device as the second chamber is being expanded;

FIG. 11F shows a trocar driven through abdominal wall and the side-top-wall window, and the removable window being removed; and FIG. 11G shows the gall bladder being treated using a laparoscopic instrument passed through the main chamber.

DETAILED DESCRIPTION OF THE INVENTION

Figure 1A:
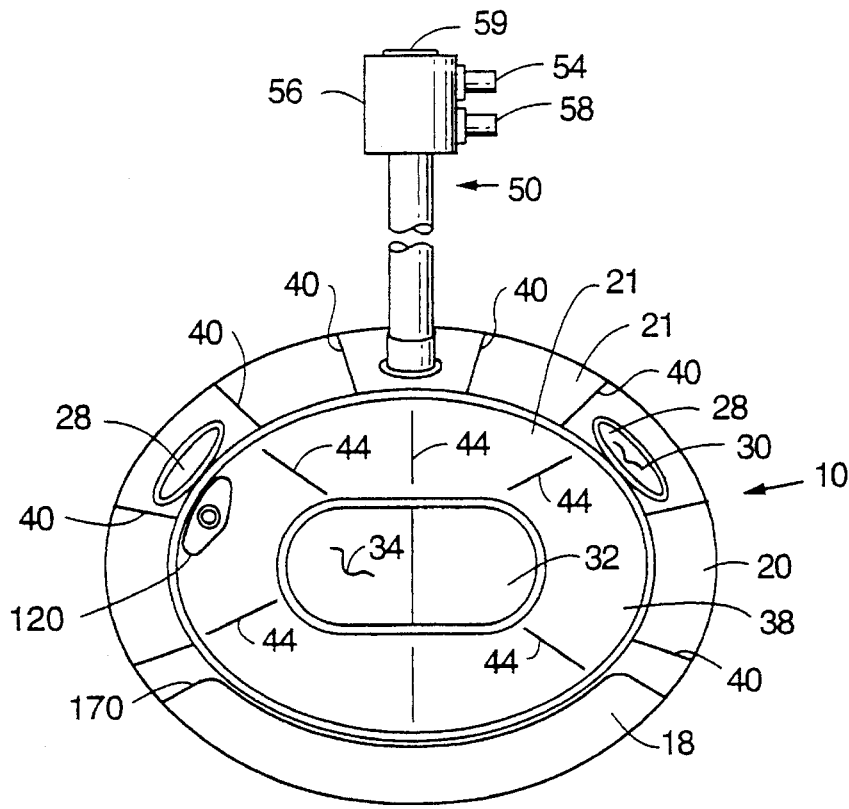
FIGS. 1A, 1B, 1C, 1D, and 1E show a top view, a front elevation, a bottom view, a side elevation, and a cross-sectional view of the preferred embodiment of the inflatable retraction device according to the invention.
Figure 1B:
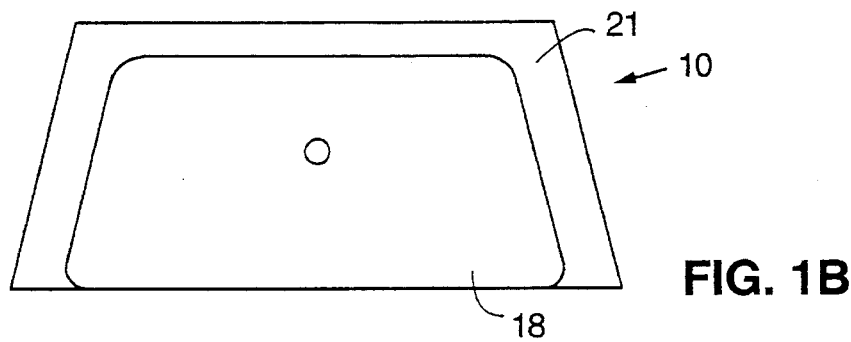

A top view, front elevation, bottom view, side elevation, and cross-sectional view of a version of the inflatable retraction device 10 according to the invention are shown in FIGS. 1A, 1B, 1C, 1D, and 1E, respectively. The shape of the inflatable retraction device shown in FIGS. 1A through 1E is optimized for bilateral hernia repair, as will be described in more detail below. It is intended that inflatable retraction devices with shapes specifically adapted for use in other procedures and in other parts of the body may be made by applying the principles to be set forth below.

As in the inflatable retraction devices described in the parent application, the inflatable retraction device 10 has two inflatable chambers: the large, main inflatable chamber 12, and the second inflatable chamber 14. Of course additional chambers could be provided as are suited for particular applications. For brevity, the main inflatable chamber and the second inflatable chamber will from now on be called the main chamber and the second chamber, respectively. Chambers described as inflatable are inflatable using a fluid, which can be a gas, such as air, or a liquid, such as saline. A gas is preferred due to the ease of evacuation.

1. Shape and Size

The shape of the main chamber 12, instead of being spherical or spheroidal as in the devices described in the parent application, is shaped to fit the space in which the inflatable retraction device is used. For example, the inflatable retraction device shown in FIGS. 1A through 1E has the general shape of the frustum of an oval cone to fit in the space bounded by the pelvis in the male abdomen, as shown in FIG. 2, in the course of repairing an inguinal hernia.

Hernia repair is carried out in the abdominal space between the umbilicus U and the pubic bone PB. The shape of the main chamber 12 (FIG. 1E) is designed to mate with the inner boundary of the pelvis P, which stabilizes the location of the inflatable retraction device during retraction. The phantom line 16 shows how the shape of the inflatable retraction device 10 fits snugly into the space bounded by the pelvis P. Adapting the shape of the inflatable retraction device to the space in which it is used in this way ensures that the inflatable retraction device will be properly located relative to the site of the hernia (or other tissue to be treated) when the retraction device is inflated.

2. Structure (a) Second Chamber

Returning now to FIGS. 1A through 1E, the size of the second chamber 14 is selected to optimize the clinical and structural functions of the device. Increasing the size of the second chamber increases the retraction force that can be exerted by the inflatable retraction device after the inflation pressure in the main chamber has been released. Increasing the size of the second chamber also reduces the inflation pressure required for the second chamber to exert a given retraction force. Thus, increasing the size of the second chamber, together with some additional improvements that will be described below, increases the reliability of the inflatable retraction device.

Increasing the size of the second chamber 14 also increases the proportion of the surface of the main envelope 15 occupied by the second chamber 14. This, in turn, reduces the area of the main envelope 15 enclosing the main chamber 12 available to provide windows in which apertures can be pierced. However, by making the inflatable retraction devices of the present invention specific to an applications or a group of application, and by providing at least one large, removable window 18 (to be described below) in a predetermined, application-specific location in the main envelope, and by providing at least one smaller, piercable window 32 in a predetermined, application-specific location in the main envelope, the advantages of increasing the size of the second chamber can be obtained while providing excellent access to the tissue to be treated.

(b) Main Chamber and Second Chamber

The side-wall part 20 of the second envelope 21 of the second chamber 14 is disposed around the side wall 22 of the main chamber 12. The side-wall part 20 of the second envelope runs substantially parallel to the side wall 22 of the main chamber between the bottom wall 24 and the top wall 26. In the embodiment shown, the side-wall part 20 of the second envelope covers all, or substantially all, of the side wall 22 of the main chamber except for the part of the side wall occupied by the removable window 18, and the side-wall window 28.

The second envelope 21 also includes the bottom-wall part 36 and the top-wall part 38, each of which respectively runs parallel to the bottom wall 24 and the top wall 26 of the main chamber 12. The bottom-wall part covers substantially all of the bottom wall of the main chamber. The top wall part covers most of the top wall of the main chamber, except for the part of the top wall occupied by the top-wall window 32.

(c) Windows

The side-wall part 20 of the second envelope 21 is shaped to expose part of the side wall 22 of the main chamber 12. The exposed part of the side wall then provides the side-wall window 28 in which one or more apertures, such as the aperture 30, can be pierced to allow instruments to pass into the main chamber to treat the tissue. The top-wall part 38 of the second envelope is also shaped to expose a part of the top wall 26 of the main chamber. The exposed part, which may be in the center of the top wall, as shown, provides the top-wall window 32 in which one or more apertures, such as the aperture 34, can also be pierced to allow instruments to pass into the main chamber to treat the tissue. The size, shape, and location of the top-wall window 32 and the side-wall window 28 may be changed from those shown depending on the application, and additional windows may be provided if required. A window may additionally or alternatively be provided at the junction of the side wall and the top wall.

It should be noted that, unlike piercing an aperture in the main envelope 15 working from inside the main chamber 12, the apertures 30 and 34, which allow instruments to pass into the main chamber, are pierced working from outside the main chamber, as will be described in detail below. Piercing an aperture working from outside the main chamber involves a considerably reduced risk of the instrument used to pierce the apeme accidentally injuring the tissue being treated.

3. Localized Stress Reduction

To increase the retraction force exerted by the second chamber 14 without an increased risk of rupturing the main envelope 15 or second envelope 21, areas of high localized stress have been systematically eliminated from the design of the envelopes of the inflatable retraction devices according to the invention. High localized stress can be a major course of premature rupturing of the envelopes of an inflatable retraction device.

(a) Baffles

In the preferred inflatable retraction devices described in the parent application, the second envelope of the second chamber is attached to the main envelope of the main chamber primarily at its periphery. This arrangement results in high localized stress at the line of attachment between the second envelope and the main envelope. To withstand this stress, the strength of both envelopes must be increased (which usually requires an increase in the thickness of the material of the envelopes, and hence of the bulk of the inflatable retraction device in its collapsed state), or the inflation pressure of the second chamber must be reduced (which reduces the retraction force that can be exerted by the inflatable retraction device when the inflation pressure of the main chamber is released, and the retraction force is provided only by the second chamber).

Figure 3A:
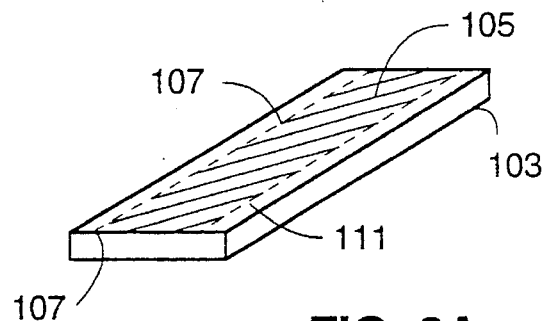
FIG. 3A shows baffle halves prior to welding.
Figure 3B:
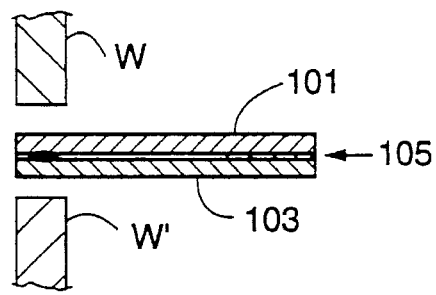
FIG. 3B shows welding the baffle halves together.
Figure 3C:
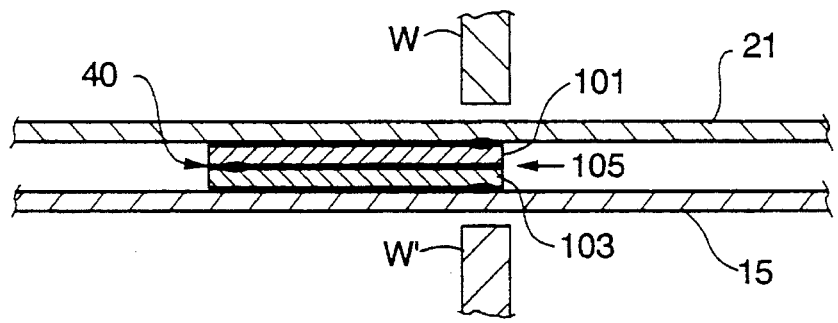
FIG. 3C shows the complete baffle being welded to the main envelope and the second envelope.
Figure 3D:
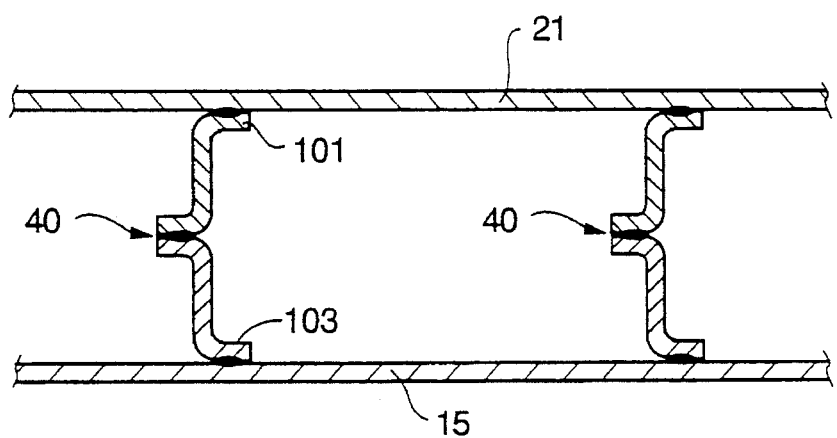
FIG. 3D shows the baffles extending between the main envelope and the second envelope in the expanded second chamber.

In the inflatable retraction device 10 according to the present invention, the second envelope 21 is attached to the main envelope 15 at its periphery, and, in addition, plural baffles, such as the baffles 40, 42, and 44, are disposed between the second envelope and the main envelope at regular intervals, as shown in FIGS. 1A through 1E, and as shown in detail in FIG. 3D. The baffles 40, 42, and 44 limit the separation of the second envelope 21 from the main envelope 15 when the second chamber is inflated. The baffles also provide plural interconnections between the main envelope 15 and the second envelope 21, which reduces the localized stress on the line of attachment between the main envelope and the second envelope when the second chamber is inflated. Thus, although the baffles require additional material, they allow the bulk of the inflatable retraction device in its collapsed state to be reduced, because they allow the main envelope and the second envelope to be made of a thinner material. Since they reduce the level of localized stress, the baffles increase the reliability of both chambers of the inflatable retraction device.

In the inflatable retraction device shown in FIGS. 1A through 1E for use in hernia repair procedures, in which the main retraction force is exerted between the top wall and the bottom wall, the baffles 40 disposed on the side wall 22 run substantially normally to the plane of the bottom wall 24 and the top wall 26. Other arrangements of the baffles on the side wall, for example, baffles running parallel to the top wall and the bottom wall, or baffles disposed at an angle to the plane of the top wall and the bottom wall, could be preferred in other applications.

Figure 1C:
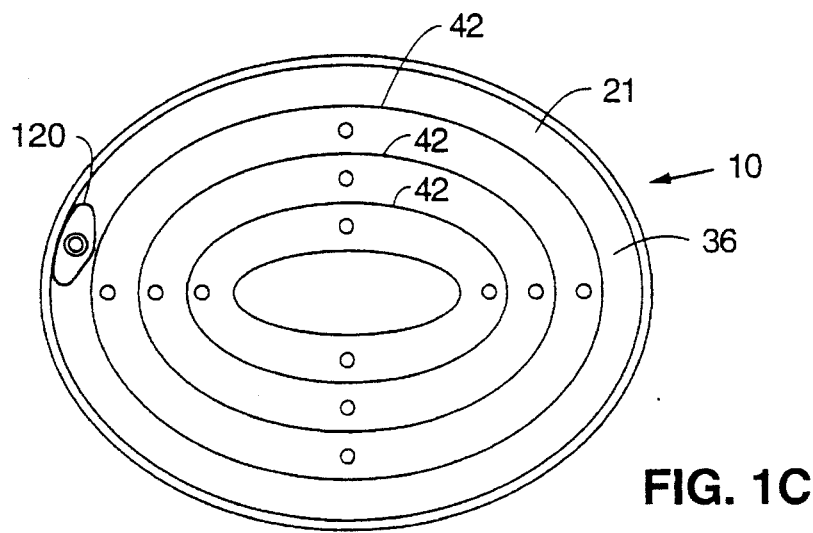
Figure 1D:
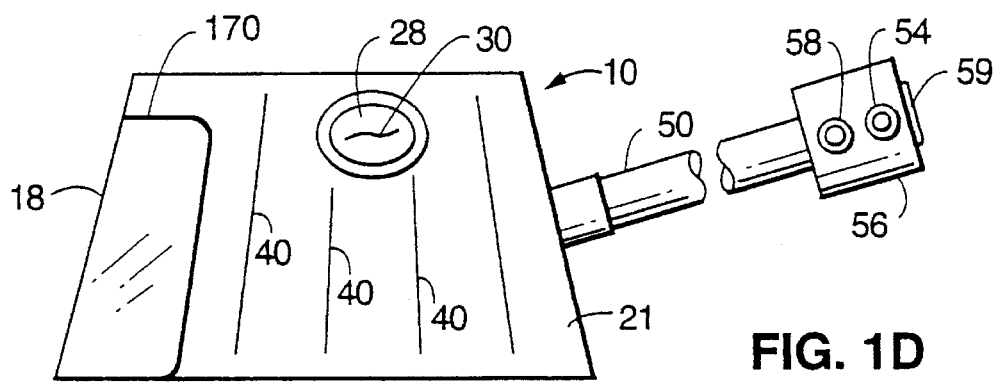

In the inflatable retraction device 10 for used in bilateral hernia repair shown in FIGS. 1A through 1E, the bottom-wall baffles 42 on the bottom wall 24 preferably run concentrically, as shown in FIG. 1C, whereas the top-wall baffles 44 on the top wall 26 run radially, as shown in FIG. 1A. In other applications, it could be preferable for both bottom-wall baffles 42 and top-wall baffles 44 to be disposed concentrically, or to be disposed radially, or for the bottom-wall baffles 42 to run radially, and the top-wall baffles 44 to run concentrically, depending on the application.

(b) Baffle Construction

The baffles 40, 42, and 44 are preferably fabricated and attached to the main envelope 15 and the second envelope 21 by the process shown in FIGS. 3A through 3D. This process attaches each baffle to the main envelope and to the second envelope using two welding operations. The two-piece baffle used in the procedure saves having to bend the baffles prior to welding, as would be required with a one-piece baffle.

The baffles 40, 42 and 44 are preferably made of the envelope material, i.e., the same material as the main envelope and the second envelope, to be described below. An example of making the baffles 40 will now be described. Each baffle is made by welding, preferably by RF welding, two baffle halves 101 and 103 together along the length of the baffle. One of the baffle halves 103 is selectively coated with a suitable welding release agent 105 as shown in FIG. 3A. The other baffle half 101 is then laid on top of the baffle half 103 between the welding electrodes W and W', as shown in the cross sectional view of FIG. 3B. The welding electrodes W and W' then weld the two baffle halves together along the length of the baffle on the phantom line 107 shown in FIG. 3A.

The completed baffle 40 is laid on the main envelope 15 between the welding electrodes W and W', as shown in the cross-sectional view of FIG. 3C. In an actual operation, plural completed baffles 40 would be laid on the main envelope 15. The second envelope 21 is then laid on the completed baffle and the main envelope. The welding electrodes W and W' then perform a second welding operation to weld the baffle 40 along the length of the baffle to the main envelope and the second envelope. For example, the second welding operation welds the baffle half 103 to the main envelope along the phantom line 111, remote from the phantom line 107, shown in FIG. 3A.

The second welding operation welds the baffle half 101 to the second envelope 21, and welds the baffle half 103 to the main envelope 15. However, because of the welding release agent 105 between the two baffle halves in the region of the weld, the second welding operation does not weld the baffle halves together. Accordingly, when the second chamber is inflated, as shown in the cross-sectional view of FIG. 3D, the second envelope 21 separates from the main envelope 15 until the baffles 40 are fully distended. The baffle halves 101 and 103 separate from one another except where they were welded along the line 107 (FIG. 3A) in the first welding operation.

(c) Interconnection Chamber

During inflation of the second chamber 14 (FIG. 1E), provision must be made for the inflation fluid to pass from the side-wall part 20 of the second chamber 14, where the inflation fluid (gas, liquid, etc. ) enters the second chamber, to the bottom-wall part 47 and the top-wall part 48 of the second chamber. This was not a consideration in the inflatable retraction devices described in the parent application, because the preferred embodiment of the second chamber was not divided into a side-wall, bottom-wall, and top-wall portions.

A known way of making a provision for the inflation fluid to pass from the side-wall part 20 of the second chamber 14 to the bottom-wall part 47 and the top-wall part 48 of the second chamber is to weld a small part of the first envelope covered by the top-wall part of the second chamber to a small part of the main envelope covered by the side-wall part of the second chamber. A hole is pierced through the welded portion of the main envelope to connect the top-wall part of the second chamber to the side-wall part of the second chamber. A similar arrangement is used to connect the bottom-wall part of the second chamber to the side-wall part of the second chamber. With this arrangement, the parts of the main envelope that are welded together can pull apart when the second envelope is inflated. This produces a high level of stress localized at the welds, and, consequently, the welds are a potential rapture site for both the main chamber and the second chamber.

Figure 4A:
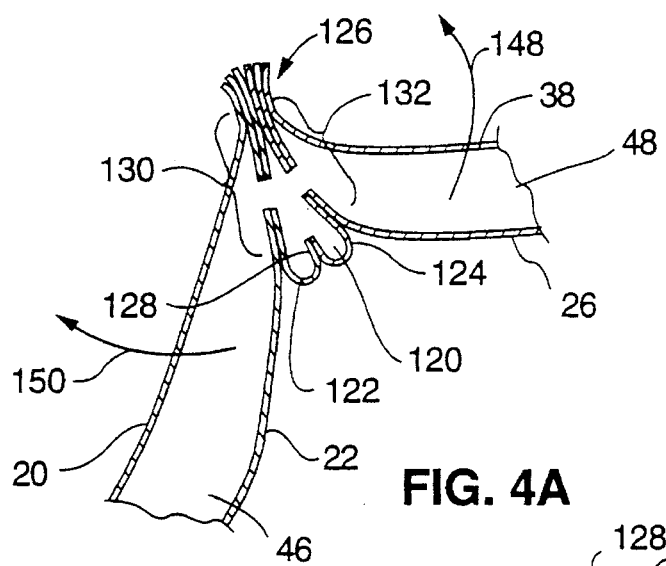
FIG. 4A shows the preferred form of the junction between the top-wall part and the side wall part of the second chamber. The junction includes the interconnection chamber.
Figure 4B:
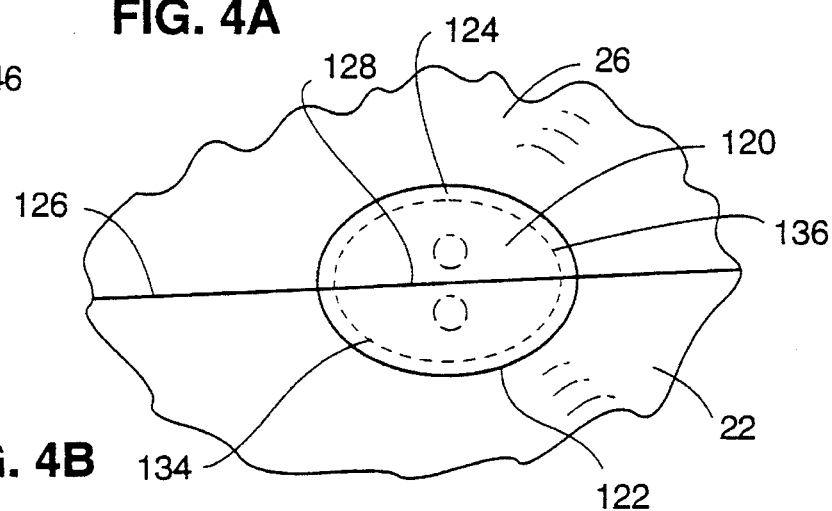
FIG. 4B is a view of the interconnection chamber at the junction of the side wall and the top wall looking outwards from inside the main chamber.
Figure 4C:
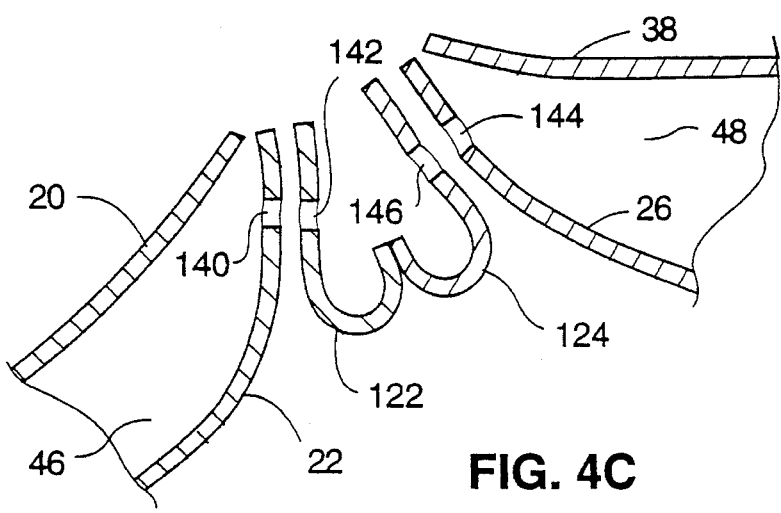
FIG. 4C is an exploded view of the preferred form of the junction between the top-wall part and the side wall part of the second chamber.

To avoid high levels of localized stress in the inflatable retraction device according to the invention, provision is made for inflation fluid to flow from the side-wall part 46 of the second chamber to the bottom-wall part 47 of the second chamber and the top-wall part 48 of the second chamber via the interconnection chambers 120 shown in FIGS. 1A, 1C, 4A, 4B, and 4C. FIG. 4A shows a cross-sectional view of the preferred form of the junction between the side wall and the top wall of the inflatable retraction device. FIG. 4B is a view of the interconnection chamber 120 at the junction of the side wall and the top wall looking outwards from inside the main chamber 12. FIG. 4C shows an exploded view of the junction.

At the junction, the side wall 22 and the top wall 26 of the main chamber 12, and the side wall part 20 and the top wall part 38 of the second envelope are all welded together along the line 126. Also included in the weld are the two envelope halves 122 and 124 enclosing the interconnection chamber 120. The two envelope halves 122 and 124 are also welded together along the line 128, remote from the weld line 126, to form the interconnection chamber prior to welding the interconnection chamber to the main and second envelopes.

The side wall 22 of the main chamber 12 includes the inflation fluid passage 140 corresponding to the inflation fluid passage 142 in the envelope half 122. The top wall 26 of the main chamber includes the inflation fluid passage 144 corresponding to the inflation fluid passage 146 in the envelope half 124.

The envelope half 122 is welded to the side wall 22 of the main chamber in the region indicated by the reference numeral 130 (the boundary of the weld area is shown in FIG. 4B by the phantom line 134), so that the inflation fluid passages 140 and 142 are aligned with one another. The envelope half 124 is welded to the top wall 26 of the main chamber in the region indicated by the reference numeral 132 (the boundary of the area is shown in FIG. 4B by the phantom line 136) so that the inflation fluid passages 144 and 146 are aligned with one another.

When the inflatable retraction device is in its collapsed state, the inflation fluid passages 140, 142, 144, and 146 are all aligned with one another. When the main chamber 12 of the Eatable retraction device is inflated, portions of the main envelope 15 move apart from one another. In particular, the part 130 moves apart form the part 132 as the top wall 26 and the side wall 22 move in the directions indicated by the arrows 148 and 150, respectively. The shape of the interconnection chamber 120 changes to accommodate this movement with little stress on the welds between the interconnection chamber and the main envelope.

When the second chamber 14 is inflated, inflation fluid passes from the side-wall part 46 of the second chamber to the top wall part 48 of the second chamber by passing through the interconnected inflation fluid passages 140 and 142 into the interconnection chamber. Inflation fluid then passes through the interconnected inflation fluid passages 144 and 146 into the top-wall part of the second chamber. Thus, provision is made for inflation fluid to pass from the side-wall part 46 of the second chamber to the top wall part 48 of the second chamber with litfie localized stress on the main and second envelopes.

4. Envelope Material

To minimize the volume of the Eatable retraction device in its collapsed state, a new envelope material has been developed for the parts of the inflatable retraction device made of envelope material, i.e., the main envelope, the second envelope, the baffles, and the envelope halves of the interconnection chamber. When used with the localized stress reduction techniques described above, films of the new envelope material as thin as 2–3 mil (50–75 μm) are sufficiently strong to withstand the inflation pressures of both the main chamber and the second chamber.

Figure 5:
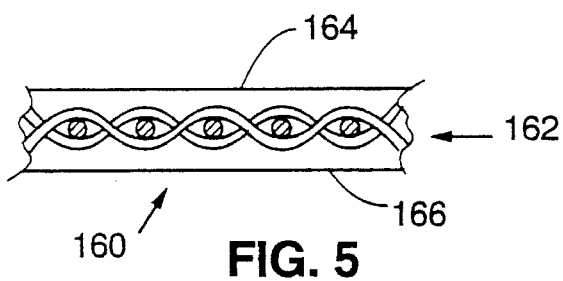
FIG. 5 is a cross sectional view of a small piece of the envelope material according to the invention.

A cross sectional view of a small piece of the new envelope material 160 is shown in FIG. 5. Polyester has desirable strength characteristics for use as the envelope material, but polyester is otherwise less desirable: it is relatively rigid, and crinkles easily. Moreover, polyester is difficult, if not impossible, to weld. RF welding is the preferred method of connecting the envelope material in the inflatable retraction devices according to the invention. Other suitable bonding techniques could also be used.

Polyurethane has characteristics that make it suitable for use in instruments contacting parts of the human body. It is soft, supple, non-abrasive, and is easy to weld. However, its tensile strength is not as good as that of polyester.

The envelope material is a composite material that exploits the advantages of both polyester and polyurethane. To bond polyurethane successfully to polyester (bonding a polyurethane film to a polyester film would be very difficult), the nylon or polyester fabric layer 162 about 0.5 to 2 mil. (12–50 μm) thick is used as the core of the envelope material 160. The nylon or polyester fabric layer 162 could be a woven fabric as shown in FIG. 5, or could be a layer of randomly-oriented polyester or nylon fibres. The nylon or polyester fabric layer 162 is laminated between two polyurethane films 164 and 166 to provide a film of envelope material with a preferred thickness of 3 mil. (75 μm). The polyurethane films bond securely to the uneven surface of the nylon or polyester layer 162.

The resulting envelope material 160 is supple, soft, non-abrasive, and transparent, and is easily welded using RF welding. The envelope material also has high tensile strength and low elongation. Finally, the envelope material will fold with small radius folds, so that an inflatable retraction device made of this material can be compacted into a small volume for laparoscopic insertion into the body.

5. Removable Window

The removable window 18 will now be described in more detail. The inflatable retraction devices described in the parent application provided plural piercable windows in the envelope of the main chamber. During the retraction process, the inflatable retraction device was manipulated to locate one of the windows adjacent to the tissue to be treated. Then, working from inside the main chamber, the surgeon used a sharp instrument to cut an aperture in the window adjacent to the tissue to gain access to treat the tissue. The process of cutting the aperture in the window could require a considerable time because the surgeon had to carry out the process carefully to ensure that the insmnnent cutting the aperture did not accidentally cut the tissue to be treated.

The inflatable retraction device 10 according to the invention provides the removable window 18 to speed up the process of providing access to the tissue to be treated and to reduce the risk of accidentally cutting the tissue. Once the inflatable retraction device 10 has been deployed in the correct location in the body, it now only requires a few seconds for the surgeon to detach or otherwise displace the removable window to gain access to the tissue. In detaching the removable window from the main envelope, there is no requirement that the removable window be completely detached from the main envelope. The removable window can be partially detached from the main envelope, and the partially detached portion can be pulled out of the way to provide access to the tissue, leaving the rest of the removable window attached to the main envelope.

The inflatable retraction device according to the preferred embodiment of the invention exploits the difference in shear strength and peel strength of certain adhesives to provide a removable window that will maintain the integrity of the main chamber during the retraction process, and which can easily be removed once retraction is being maintained by the second chamber.

Figure 1E:
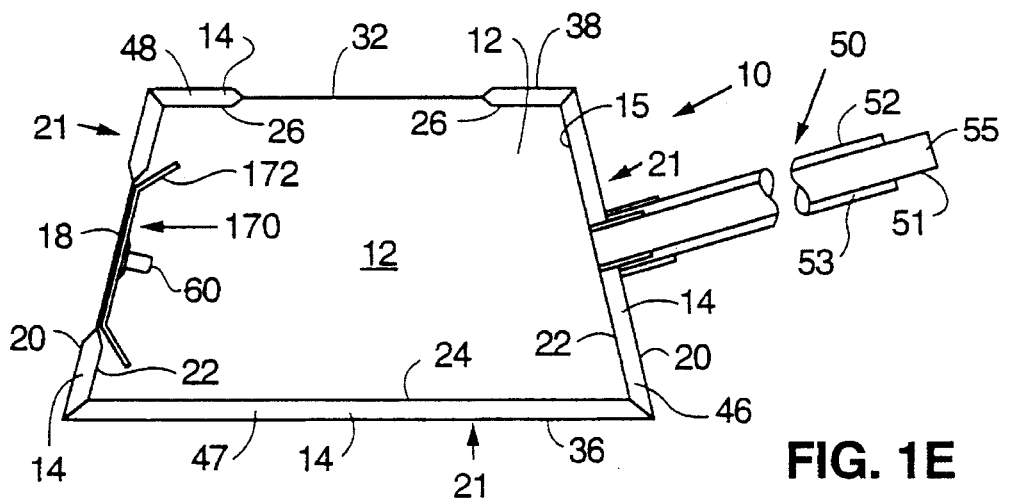
Figure 2:
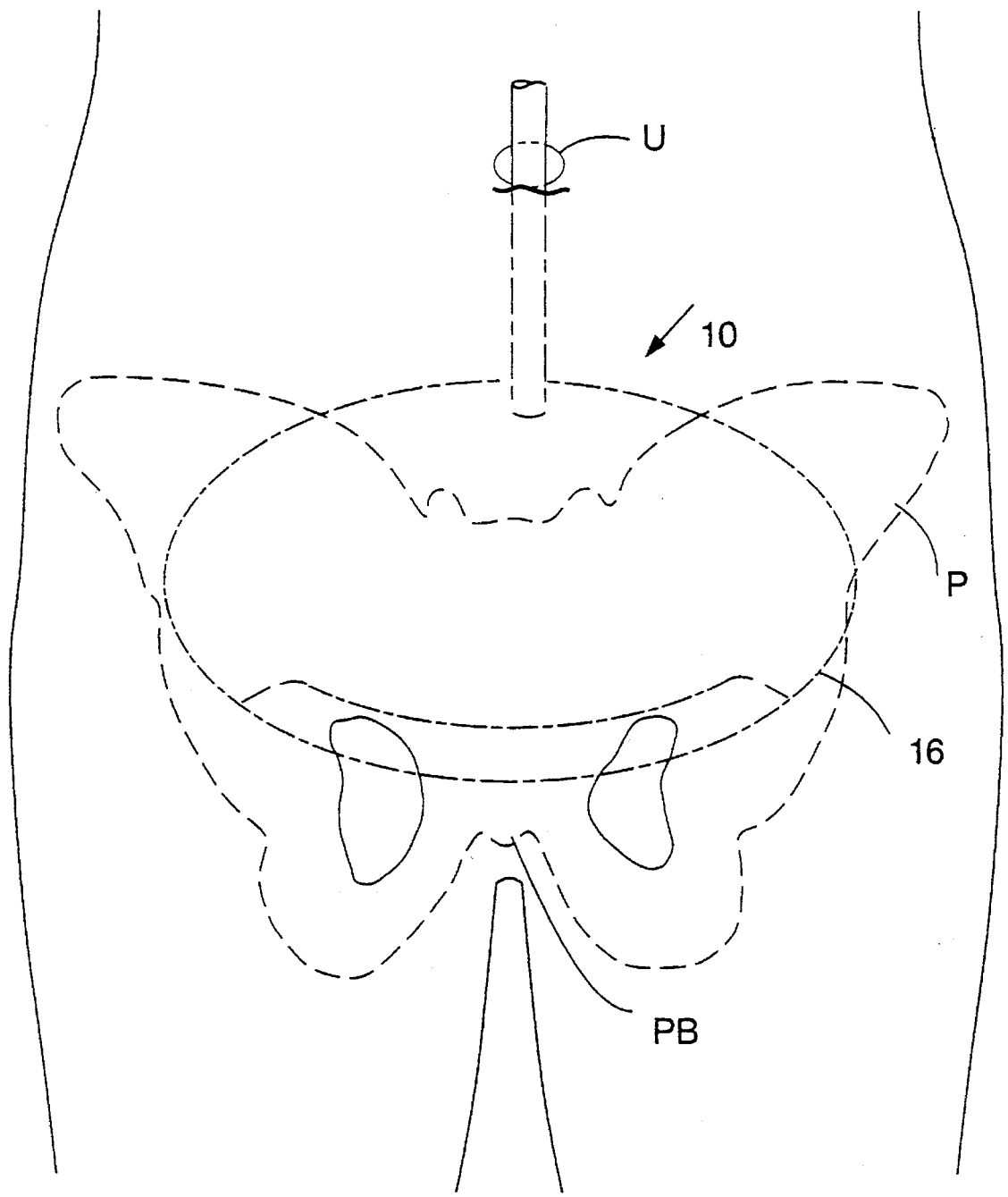
FIG. 2 shows the preferred embodiment of inflatable retraction device as it fits in the space bounded by the pelvis in the male abdomen in the course of repairing an inguinal hernia.
Figure 6A:
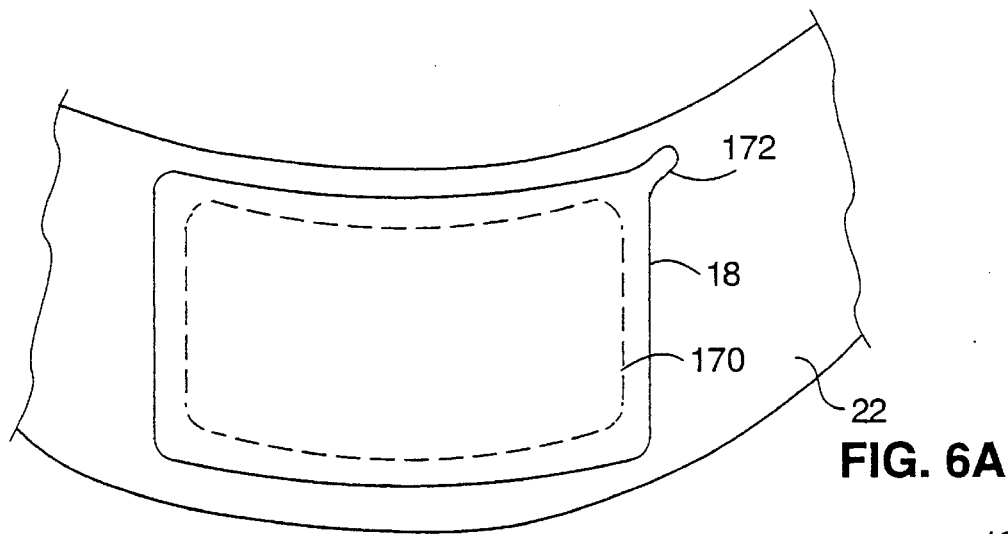
FIG. 6A is a view of the removable window from inside the main chamber.

In the inflatable retraction device 10 shown in FIGS. 1A through 1E, the side wall 22 of the main chamber 12 is formed with a large opening 170 in the location of the removable window 18. The removable window 18 is then attached to the side wall 22 to cover the opening 170. The removable window 18 is made slightly larger than the opening 170 so that it will overlap the opening 170, and includes at least one tab 172, as shown in FIGS. 1E and 6A. The tab 172 can be gripped with suitable laparoscopic forceps to remove the removable window. Until it is removed, the removable window 18 can be regarded as part of the side wall 22.

(a) Removable Window Attachment

A suitable bond between the removable window 18 and the side wall 22 can be made by welding two dissimilar materials. For example, if the side wall is made of the polyester/polyurethane composite envelope material described above, the removable window can be made of polyethylene. An RF weld forms a bond between a polyurethane side wall and a polyethylene window that has a high shear strength and a low peel strength. The high shear strength of the bond enables the removable window to act as an integral part of the side wall during expansion of the main chamber. Once the inflation pressure in the main chamber has been released after inflation of the second chamber, a suitable tab 172 can be gripped by laparoscopic forceps and the removable window can be peeled away from the side wall. The bond between the removable window and the side wall peels easily.

Figure 6B:
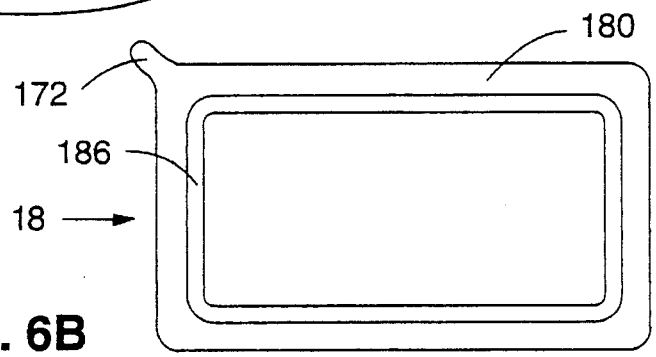
FIG. 6B is a plan view of the removable window showing the attachment frame.

An alternative construction of the bond between the removable window and the side wall is shown in FIG. 6B. The removable window 18 is fabricated from two pieces of envelope material 180 and 182 attached to one another by a layer of a suitable adhesive 184. The preferred adhesive is an acrylic adhesive: silicone and urethane adhesives also work, but less well.

Figure 6C:
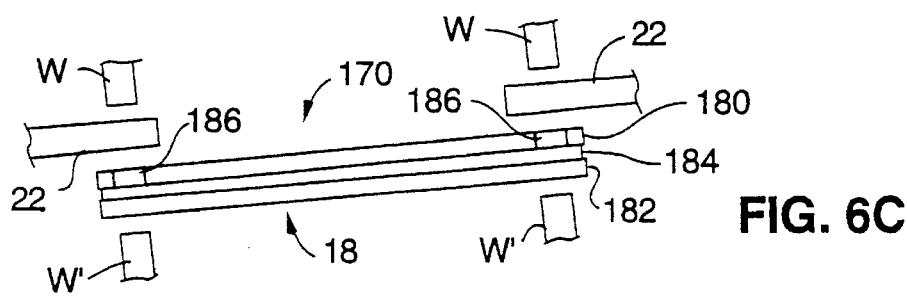
FIG. 6C shows the removable window in place adjacent the main envelope prior to welding.

The attachment frame 186 shown in FIG. 6B and 6C is then cut in the piece 180. The cut does not extend through the piece 182, however.

The removable window 18 is then laid on the side wall 22 and positioned so that the removable window covers the opening 170. The removable window and the side wall are the placed between the welding electrodes W and W', as shown in the cross-sectional view of FIG. 6C. The welding electrodes W and W' are shaped to match the shape of the attachment frame 186.

Figure 6D:
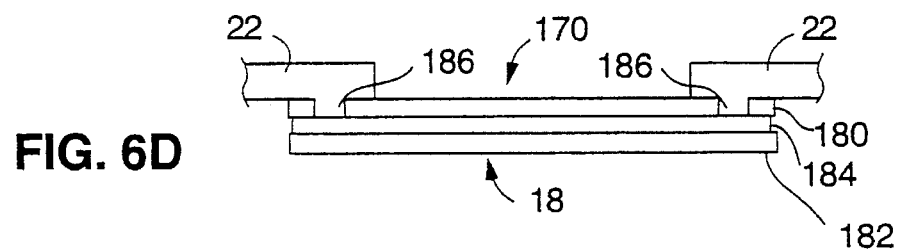
FIG. 6D shows the removable window after welding the attachment frame to the main envelope.

The welding electrodes W and W' weld the attachment frame 186 to the side wall 22, to form the structure shown in FIG. 6D in which only the attachment frame 186 is welded to the side wall 22. The rest of the removable window, i.e., the window piece 182, the adhesive 184, and window piece 180 other than the attachment frame 186, are attached to the side wall by the adhesive bond between the attachment frame 186 and the window piece 182.

The acrylic adhesive bond between the attachment frame 186 and the window piece 182 provides a high shear strength and a low peel strength. The high shear strength of the bond enables the removable window to act as an integral part of the side wall during inflation of the main chamber. Once the inflation pressure in the main chamber has been released after inflation of the second chamber, the tab 172 can be gripped by laparoscopic forceps and the removable window can be peeled away from the side wall, as described above.

Figure 6E:
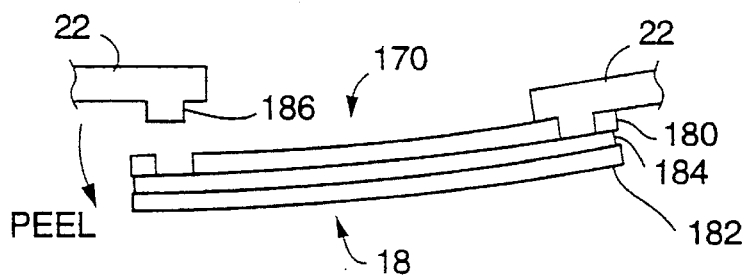
FIG. 6E shows the removable window partially peeled away from the main envelope.

FIG. 6E shows the removable window partly peeled away from the side wall 22. It can be seen that the attachment frame 186 remains attached to the side wall 22, and that the removable window parts from the side wall at the adhesive bond between attachment frame and the window piece 182. The peel strength characteristics of the acrylic adhesive enable the bond between the window piece and the attachment frame to peel apart easily, and the removable window to be removed. Alternative constructions for providing a removable or displaceable window could also be used.

(b) Application-Specific Shape and Removable Window Location

Figure 7A:
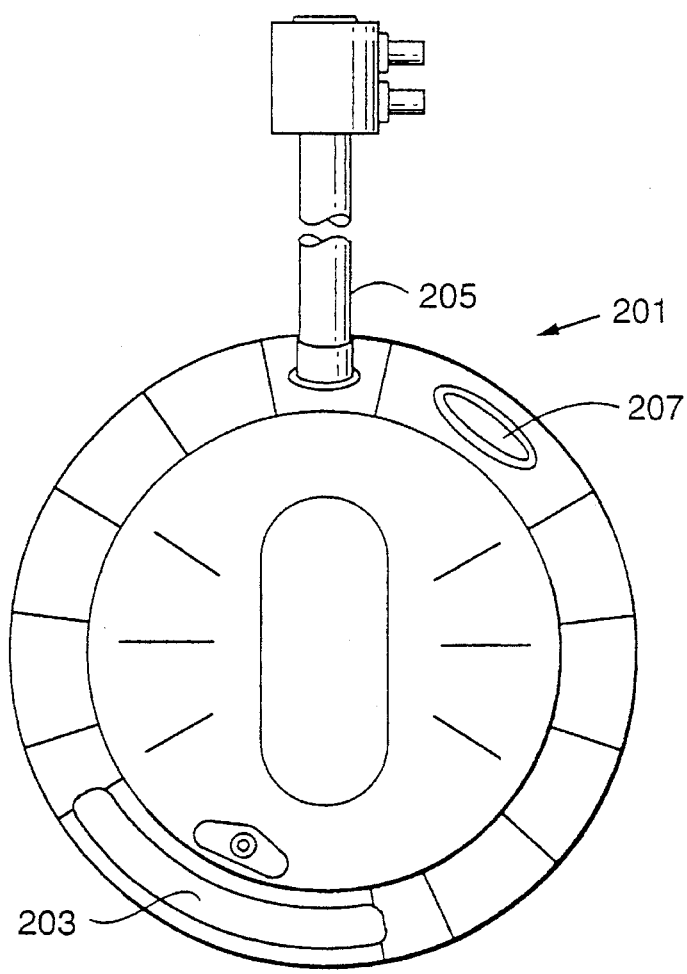
FIG. 7A is a plan view of an inflatable retraction device according to the invention with windows located for repairing hernias located on the right side of the body.
Figure 7B:
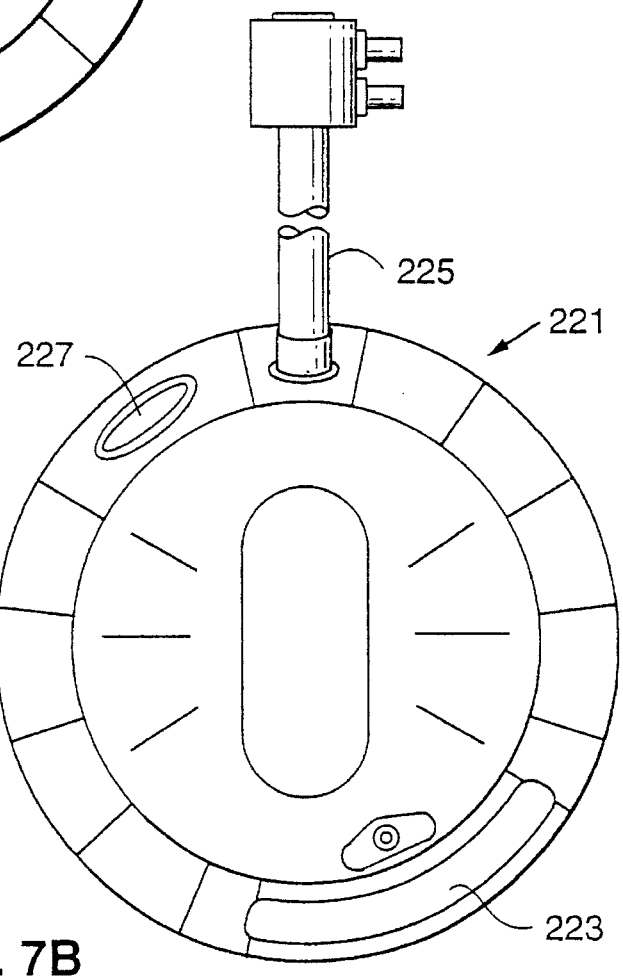
FIG. 7B is a plan view of an inflatable retraction device according to the invention with windows located for repairing hernias located on the left side of the body.

FIGS. 7A and 7B show alternative configurations of the inflatable retraction device for hernia repair shown in FIGS. 1A through 1E. The main chamber of the inflatable retraction devices shown in FIGS. 7A and 7B are asymmetrical relative to the axis defined by the inflation tube. The inflatable retraction device 201 shown in FIG. 7A is configured for a right inguinal hernia; and the inflatable retraction device 221 shown in FIG. 7B is configured for repairing a left inguinal hernia. Since the inflatable retraction devices 201 and 221 each provide access to only one hernia, the removable windows 203 and 223, respectively, are smaller than the removable window 18 shown in FIGS. 1A through 1E, which provides access to two hernias.

The removable window 203 in the inflatable retraction device 201 is offset about 30 degrees to the right of the axis defined by the inflation tube 205. With this offset, the entry of the right inguinal tube is centered on the removable window 203 when the inflatable retraction device 201 is correctly located in the lower abdomen. Also, the side window 207 is located to the left of the inflation tube 205, diametrically opposite the removable window 203.

The removable window 223 in the inflatable retraction device 221 is offset about 30 degrees to the left of the axis defined by the inflation tube 225. With this offset, the entry of the left inguinal tube is centered on the removable window 223 when the inflatable retraction device 221 is correctly located in the lower abdomen. Also, the side window 227 is located to the left of the inflation tube 225, diametrically opposite the removable window 223.

Many further variations are possible. For example, the side walls may be vertical, or curved, or non-linear. The main chamber may be more extremely asymmetrical, or may be kidney-shaped. For some applications, a spherical or spheroidal inflatable retraction having the same general construction as that described above may be optimum.

The inflatable retraction devices shown in, for example, FIG. 7A also be made with the removable window symmetrically disposed relative to the axis defined by the inflation tube. Such an inflatable retraction device would be used in procedures such as lymphadenectomy, bladder neck suspension, nephrectomy, and spine node surgery.

(c) Removable Window Size/Insufflation Trade-Off

In the inflatable retraction device shown in FIGS. 1A through 1E for repair of bilateral hernias, the removable window 18 extends from the bottom wall 24 to the top wall 26 of the main chamber, and occupies about one third of the side wall 22 of the main chamber. The large size of the removable window 19 considerably reduces the retraction force that can be exerted by the second chamber in the retraction device 10 compared with the retraction force that can be exerted by the second chambers of the inflatable retraction devices 201 and 221 shown in FIGS. 7A and 7B. Accordingly, the inflatable retraction device shown in FIGS. 1A through 1E is preferably normally used in procedures in which the properitoneal space is insufflated. The pressure of the insufflation gas provides part of the retraction force, and thus assists the second chamber 14 to provide retraction, as will be described in more detail below.

Alternatively, inflatable retraction devices according to the invention may be used without insufflation. The inflatable retraction devices 201 and 221 shown in FIGS. 7A and 7B are intended for repair of single hernias, and their removable windows 203 and 223 are considerably smaller than the removable window 18. The smaller removable window allows the second chamber to be proportionately larger, with the result that the inflatable retraction devices 201 and 221 can be used without insufflation.

6. Main Chamber Pressure Control

Referring once more to FIGS. 1A through 1F, the reliability of the main chamber 12 is increased by limiting the maximum inflation pressure in the main chamber during inflation of the second chamber. Inflation of the second chamber reduces the volume of the main chamber, and hence increases the pressure in the main chamber. Allowing the pressure in the main chamber to rise too far can lead to the main envelope rapturing.

(a) Inflation tube

The main chamber 12 and the second chamber 14 are expanded by inflation fluid passed through the inflation tube 50. The inflation robe is a coaxial arrangement of the inner inflatable tube 51 and the outer inflation robe 52. The port 56 mounted on the proximal end of the inflation robe 50 carries the pressure control valve 54 and the one-way valve 58. The port 56 also comes a flap valve 59 that seals the bore of the inner inflation robe 51, and also forms a gas-tight seal with insmmaents or the insertion shaft 62 passing through the flap valve into the main chamber 12.

The main chamber is expanded by inflation fluid passed through the pressure control valve 54 into the bore 55 of the inner inflation tube 51. The second chamber is expanded by inflation fluid passed through the one-way valve 58 into the lumen 53 between the outer inflation tube and the inner inflation robe.

In the inflatable retraction devices described in the prior application, the main chamber is expanded with inflation fluid passed through a one-way valve similar to the one-way valve 58. The one-way valve 58 is, for example, a duckbill valve. A one-way valve maintains the main chamber 12 in its expanded state after the source of inflation fluid (not shown) has been disconnected from the one-way valve. However, a normal one-way valve allows the pressure in the main chamber to increase when the second chamber 14 is expanded, and the pressure in the main chamber can to rise to a level that could impair the reliability of the main chamber.

To avoid the possibility just described, the port 56 of the inflatable retraction device 10 according to the invention is fitted with the pressure control valve 54 according to the invention. During expansion of the second chamber 14, the pressure control valve 54 prevents the pressure in the main chamber 12 from exceeding a level that could impair the reliability of the main chamber.

(b) Pressure Control Valve Construction & Operation

Figure 8A:
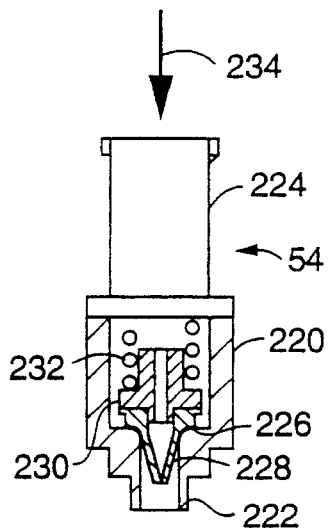
FIG. 8A shows the preferred embodiment of a pressure control valve according to the invention with a fixed release pressure.

Construction of the pressure control valve 54 according to the invention is shown in FIG. 8A. In the pressure control valve 54, the valve body 220 includes the portion 222 adapted for attachment to the port 56, and the female luer lock 224 to which the source of inflation pressure may be attached.

Formed in the valve body 220 is the valve seat 226 adapted to receive the duckbill valve 228. Fitting into the face of the duckbill valve 228 remote from the valve seat 226 is the spring adaptor 230, which keeps the duckbill valve aligned with the compression spring 232. The compression spring acts between the spring adaptor 230 and the valve body 220, and forces the duckbill valve into contact with the valve seat 226.

When inflation fluid flows into the valve in the direction of the arrow 234, the pressure of the inflation fluid causes the inflation fluid to flow through the duckbill valve 228. The compression spring 232 and the pressure of the inflation fluid keep the duckbill valve in contact with the valve seat 226. Under these conditions, the pressure inside the main chamber is exclusively determined by the pressure of the source of inflation fluid.

When the source of inflation fluid is removed from the female luer lock 224, the duckbill valve 228 closes, and the duckbill valve is kept in contact with the valve seat 226 by the compression spring 232. Consequently, inflation fluid cannot escape through the pressure control valve 54, so the pressure inside the main chamber (assuming that it is less than the release pressure of the valve) remains at about the pressure imposed by the source of inflation fluid.

When the second chamber 14 is expanded, and the pressure in the main chamber 12 rises above the release pressure of the pressure control valve 54, the pressure of the inflation fluid acting on the duckbill valve 228 overcomes the force exerted on the duckbill valve by the compression spring 232. This forces the duckbill valve away from the valve seat 226, which releases inflation fluid from the main chamber. Thus, the pressure control valve prevents the pressure in the main chamber from rising above a level that could impair the reliability of the main chamber.

It should be noted that the pressure control valve 54 does not prevent the pressure inside the main chamber 12 from rising above the release pressure of the valve when the main chamber is connected to the source of inflation fluid (not shown). However, it is acceptable to subject the main chamber 12 to pressures higher than the valve release pressure for short times during the retraction process. After the retraction is completed, and the source of inflation fluid is removed from the pressure control valve, the pressure control valve maintains the pressure in the main chamber at a level that the main chamber can reliably sustain for a prolonged period of time.

(c) Pressure Control Valve-Alternative Embodiments

Figure 8B:
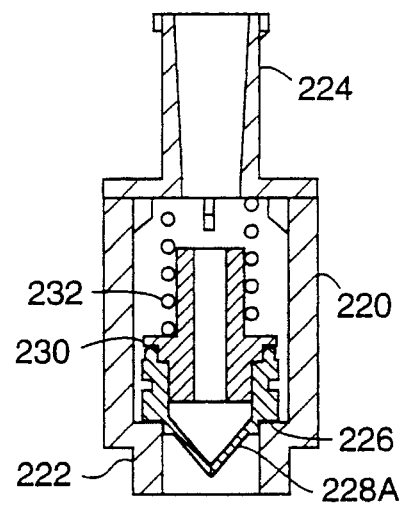
FIG. 8B shows a fast alternative embodiment of a pressure control valve according to the invention with a fixed release pressure.
Figure 8C:
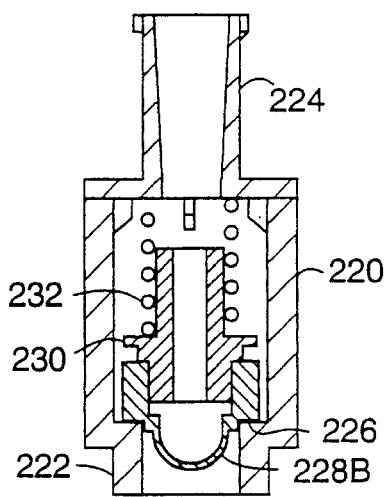
FIG. 8C shows a second alternative embodiment of a pressure control valve according to the invention with a fixed release pressure.

The release pressure of the pressure control valve 54 is determined by the force exerted by the compression spring 232 and the effective area of the duckbill valve 228. The release pressure can therefore be changed by changing the rate of the compression spring 232, or by increasing the area of the duckbill valve. FIG. 8B shows a version of the valve with the duckbill valve 228A, with a larger area than the duckbill valve 228 in FIG. 8A. All the other components in the valve shown in FIG. 8B are similar to corresponding components in FIG. 8A, and are marked with the same reference numerals. FIG. 8C shows a version of the pressure control valve with the duckbill valve 228B, which is differently shaped and has a larger area than the duckbill valve 228 in FIG. 8A. All the other components in the valve shown in FIG. 8C are similar to corresponding components in FIG. 8A, and are marked with the same reference numerals.

(d) Pressure Control Valve—Adjustable Embodiments

Figure 8D:
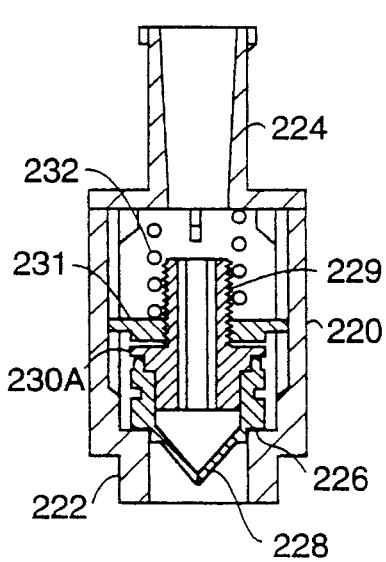
FIG. 8D shows a fast embodiment of a pressure control valve according to the invention with a variable release pressure.
Figure 8E:
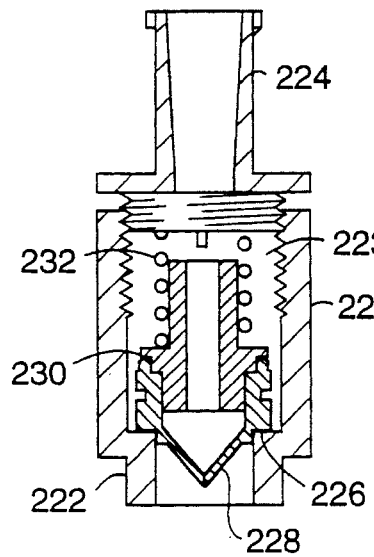
FIG. 8E shows a second embodiment of a pressure control valve according to the invention with a variable release pressure.
Figure 8F:
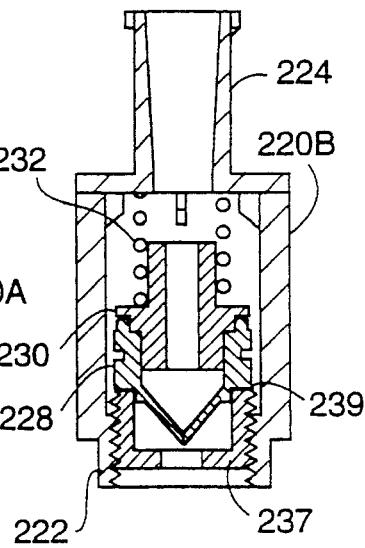
FIG. 8F shows a third embodiment of a pressure control valve according to the invention with a variable release pressure.

The release pressure of the pressure control valve according to the invention can be made adjustable, as shown in FIGS. 8D through 8F. These versions use screw mechanism acting on the compression spring 232 to enable the force exerted by the compression spring to be adjusted to provide an adjustable release pressure. This allows a common pressure control valve to be used with inflatable retraction devices with different maximum pressures.

In FIGS. 8D through 8F, components similar to those in FIG. 8A are marked with the same reference numerals. In FIG. 8D, the spring adaptor 230A includes a threaded portion 229 that engages with the threaded collar 231, on which the compression spring 232 rests. The rest of the valve is similar to the valve described above in connection with FIG. 8A, and will not be described again here. The release pressure of the valve is adjusted by rotating the threaded collar 231 relative to the spring adaptor 230A. This changes the axial position of the threaded collar on the spring adaptor, which changes the force exerted by the compression spring.

In FIG. 8E, the upper part of valve body 220A includes the threaded portion 233 which is fitted with the threaded sleeve 235 on which the end of the compression spring 232 remote from the spring adaptor 230 rests. The release pressure of the valve is adjusted by rotating the threaded sleeve 235 in the valve body 220A. This changes the axial position of the threaded sleeve in the valve body, which changes the force exerted by the compression spring.

In FIG. 8F, the lower part of the valve body 220B includes the threaded portion 239, which is fitted with the threaded valve seat 237 on which the duckbill valve 228 seam. The release pressure of the valve is adjusted by rotating the threaded valve seat 237 in the threaded portion of the valve body 220B. This changes the axial position of the threaded valve seat, the duckbill valve 228, and the spring adaptor 230, which changes the force exerted by the compression spring.

It should be noted that the adjustment of the variable pressure control valves shown in FIGS. 8D and 8E is accessible when the pressure control valve is installed on the port 56. The relief pressure of these valves can therefore be adjusted by the user. On the other hand, the variable pressure control valve shown in FIG. 8F is not accessible when the pressure control valve is installed in the port 56. This configuration of valve is useful because its relief pressure can be set by the manufacturer, and cannot be changed to an inappropriate setting by the user.

7. Inflatable Retraction Device Packaging

Figure 9A:
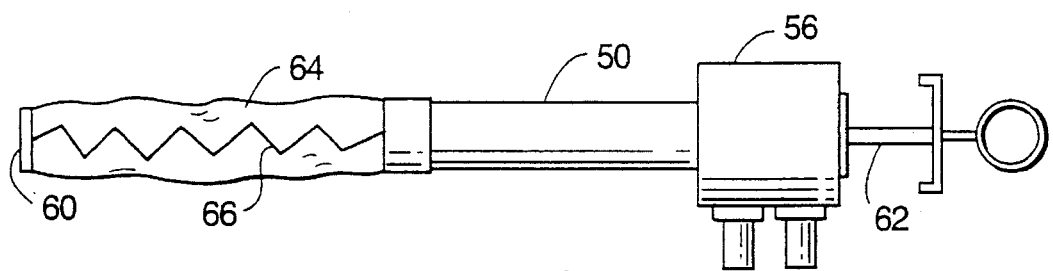
FIG. 9A is a side view of the inflatable retraction device according to the invention packaged for insertion into the body.

The inflatable retraction device 10 shown in FIGS. 1A through 1E is packaged for use in a hernia repair procedure as shown in FIG. 9A. Packaging the inflatable retraction device in this way allows the inflatable retraction device to be inserted into an incision at the umbilious; allows the packaged device to be used to dissect the peritoneum away from the properitoneal fat layer; allows the device to be correctly located in the lower abdominal region; and allows the surgeon to center the removable window 18 (FIG. 1A) on the site of the hernia by feel.

Figure 1F:
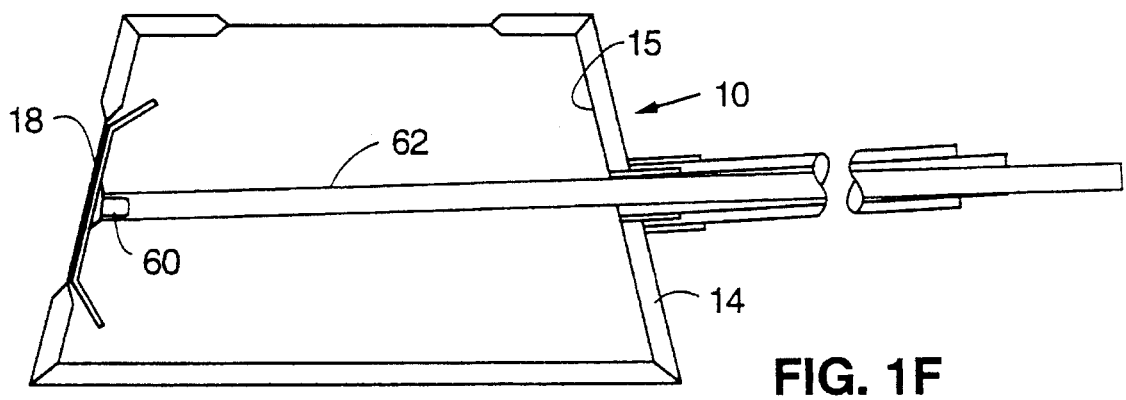
FIG. 1F shows a cross sectional view of the preferred embodiment of the inflatable retraction device with the insertion shaft in place.

FIGS. 1E and 1F show the button 60 located in the middle of the removable window 18. The button connects the distal end of the insertion shaft 62, shown in detail FIGS. 9F and 9G, to the center of the removable window 18. This allows the surgeon to use the insertion shaft 62 to control the location of the center of the removable window 18 relative to the site of the hernia during the insertion process, which will be described in detail below.

The center of the button 60 may be made optically flat, or may be given some other known optical characteristic. An endoscope E can then be inserted through the bore of the insertion shaft 62, as shown in FIG. 9C, to show the location of the center of the removable window 18 during the insertion procedure. Alternatively, the button 60 can be formed to include a female receptacle 63 adapted to receive the distal end of an endoscope E directly without the insertion shaft 62, as shown in FIG. 9H. The endoscope can be a normal-size endoscope, or a miniature endoscope similar to that shown in FIG. 9C. The receptacle 63 sized according to the endoscope used. The endoscope can be used to position the window on the desired tissue.

Figure 9B:
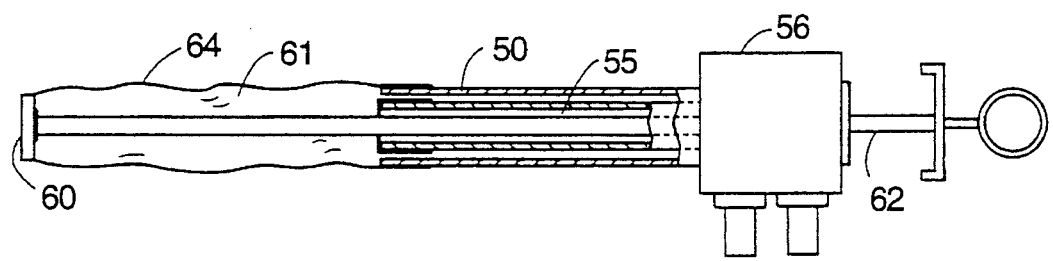
FIG. 9B is a longitudinal cross sectional view of the inflatable retraction device according to the invention packaged for insertion into the body.
Figure 9C:
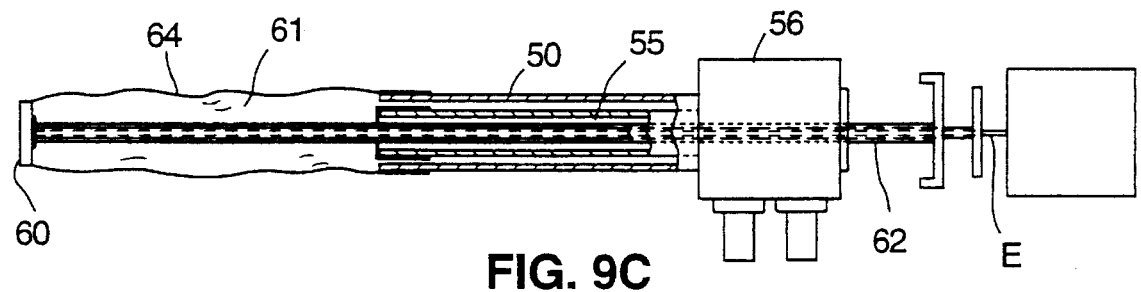
FIG. 9C is a longitudinal cross sectional view of the inflatable retraction device according to the invention packaged for insertion into the body with an endoscope inserted into the insertion shaft.
Figure 9D:
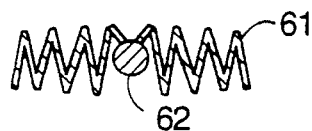
FIG. 9D is a transverse exploded view of an alternative way of arranging the envelope material relative to the insertion shaft.

When the inflatable retraction device is packaged, the insertion shaft 62 is inserted through the port 56 on the inflation tube 50, through the bore 55 of the inflation tube, and through the main chamber to engage the distal end of the insertion shaft with the button 60, as shown in the longitudinal cross-sectional view of FIG. 9B. The envelope material portion 61 of the inflatable retraction device, i.e., the main envelope, second envelope, bees, etc, are then pulled proximafly, i.e., towards the port 56, and are wrapped around the distal part of the insertion shaft. The envelope material 61 wrapped around the insertion shaft 62 forms a distal extension of the inflation tube 50, and has substantially the same diameter as the inflation tube. Alternatively, the envelope material of the inflatable retraction device may be pulled back towards the port 56, and then folded in concertina folds on either side of the insertion shaft 62, as shown in the exploded lateral cross-sectional view of FIG. 9D.

In the preferred embodiment, the envelope material is retained in its wrapped or folded state by a detachable sheath 64 that is held together using removable lacing 66, as shown in FIG. 9A. An extension (not shown) of the removable lacing passes up the outside of the inflation tube 50 to an anchor point on the port 56. The port remains outside the body when the inflatable retraction device is in position in the abdomen. Prior to expanding the main chamber, the surgeon removes the removable lacing from the detachable sheath by pulling on the extension (not shown) of the removable lacing attached to the port 56. Part of the removable lacing remains attached to the detachable sheath 64 after the removable lacing has been removed to release the detachable sheath from the packaged inflatable retraction device. This attached part enables the detachable sheath to be extracted from the body by pulling on the removable lacing.

Figure 9E:
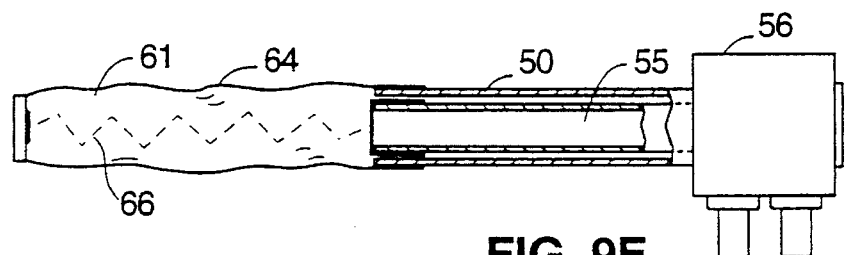
FIG. 9E is a longitudinal cross sectional view of the inflatable retraction device according to the invention packaged for insertion into the body without an insertion shaft.

The inflatable retraction device may additionally be packaged without the insertion shaft 62, as shown in the longitudinal cross sectional view of FIG. 9E. In this, the envelope material portion of the inflatable retraction device is rolled, or folded in concertinn folds such that it forms a distal extension of the inflation tube 50. The envelope material is packaged such that the button 60 in the center of the removable window is at the distal-most point of the package. The envelope material is retained in its rolled or folded state by the detachable sheath 64 held together by removable lacing 66, as described above, or by other suitable techniques.

Figure 9F:
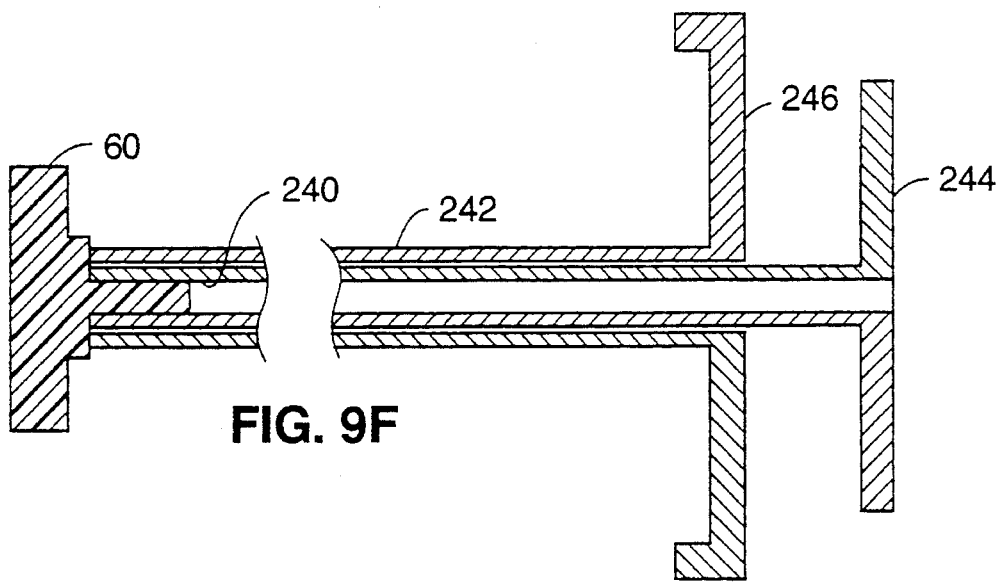
FIG. 9F is a cross-sectional view of a first embodiment of the insertion shaft according to the invention.
Figure 9G:
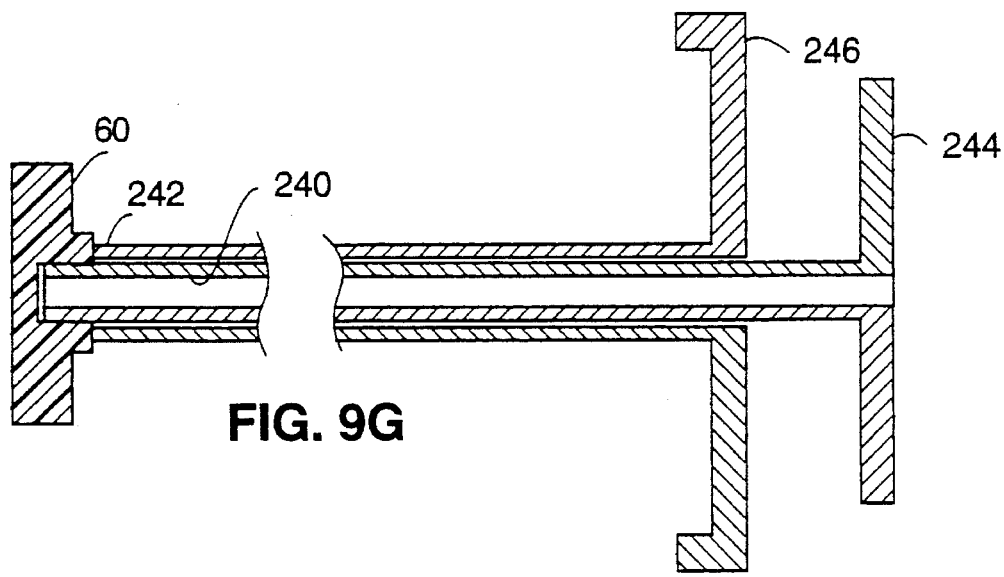
FIG. 9G is a cross-sectional view of a second embodiment of the insertion shaft according to the invention.
Figure 9H:
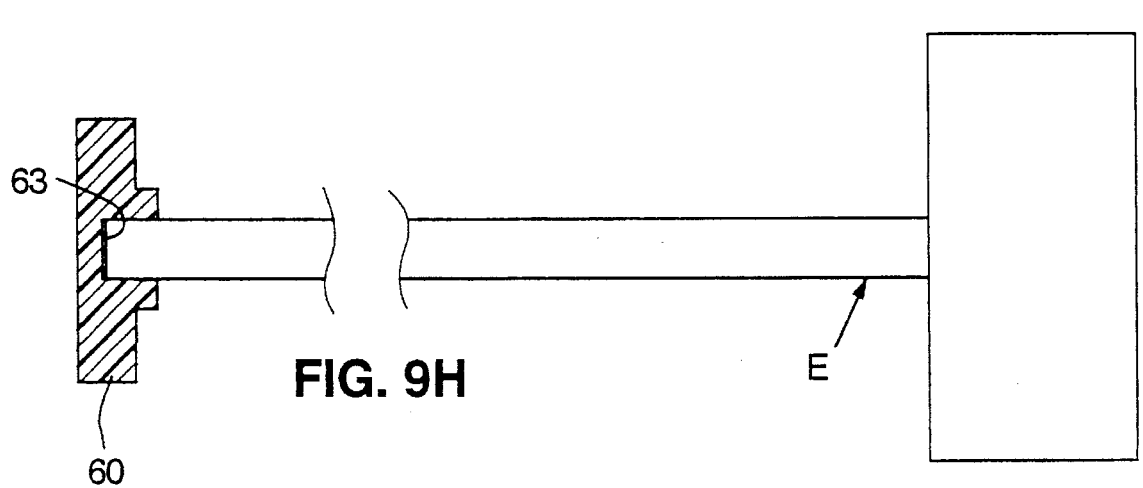
FIG. 9H is a cross sectional view of an alternative embodiment of the button adapted for accepting the distal end of an endoscope.

Alternative constructions of the insertion shaft is shown in FIGS. 9F and 9G. In both alternative constructions, the insertion shaft consists of two concentric tubes, the attachment tube 240, which attaches to the button 60 in the center of the removable window 18 (FIG. 1E), and the release tube 242, which detaches the attachment tube 240 from the button when the surgeon wishes to withdraw the insertion shaft from the retraction device. In the arrangement shown in FIG. 9F, the attachment cube 240 fits over the outside of the button 60, and the release cube 242 runs inside the attachment tube. The release tube 242 may be solid; however, if the insertion shaft is to accommodate an endoscope for observing the location of the removable window during the insertion process, the release cube must be hollow. The surgeon squeezes the release button 244 towards the finger grips 246 to release the insertion shaft from the button 60.

In the arrangement shown in FIG. 9G, the attachment cube 240, fits inside the button 60, and the release cube 242 runs outside the attachment tube. The attachment tube 240 may be solid; however, if the insertion shaft is to accommodate an endoscope for observing the location of the removable window during the insertion process, the attachment tube must be hollow. The surgeon again squeezes the release button 244 towards the finger grips 246 to release the insertion shaft from the button 60.

Alternatively, an endoscope can be used as the insertion shaft, and is inserted into the button receptacle 63 at its distal end, as shown in FIG. 9H. The receptacle 63 is optically correct, to allow clear viewing through the endoscope to the external tissue.

8. Hernia Repair Procedure

Use of inflatable retraction device according to the invention and shown in FIGS. 1A through 1E in a bilateral hernia repair procedure will now be described with reference to FIGS. 10A through 10K as an example of the use of the inflatable retraction device in a procedure involving blunt dissection. A similar method can be used in other procedures involving blunt dissection. If the patient only has a single hernia, one of the inflatable retraction devices shown in FIGS. 7A and 7B may be used instead of the inflatable retraction device shown in FIG. 1A through 1E. Choice between the devices shown in FIGS. 7A and 7B should be made in accordance with whether the hernia to be repaired is on the left or the right, as described above in connection with FIGS. 7A and 7B. When an inflatable retraction device shown in FIGS. 7A or 7B is used, the insufflation step, described below, may be omitted. The insufflation step may also be omitted using the inflatable retraction device shown in FIGS. 1A through 1E.

Figure 10A:
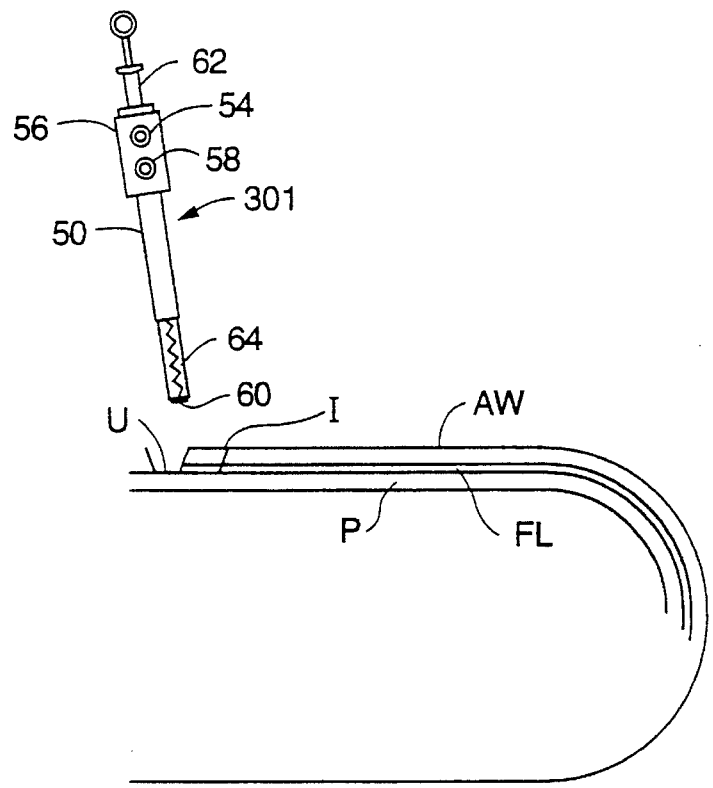
FIGS. 10A through 10K illustrate the properitoneal hernia repair procedure according to the invention.

A small incision I is made in the abdominal wall at the umbilicus. The incision is made through all the layers of the abdominal wall AW except the peritoneum P, as shown in FIG. 10A. The distal tip of the inflatable retraction device 300, which is the inflatable retraction device 10 shown in FIGS. 1A through 1E packaged as shown in FIG. 9A, is inserted into the incision until the button 60 at the distal tip of the package contacts the peritoneum P.

Figure 10B:
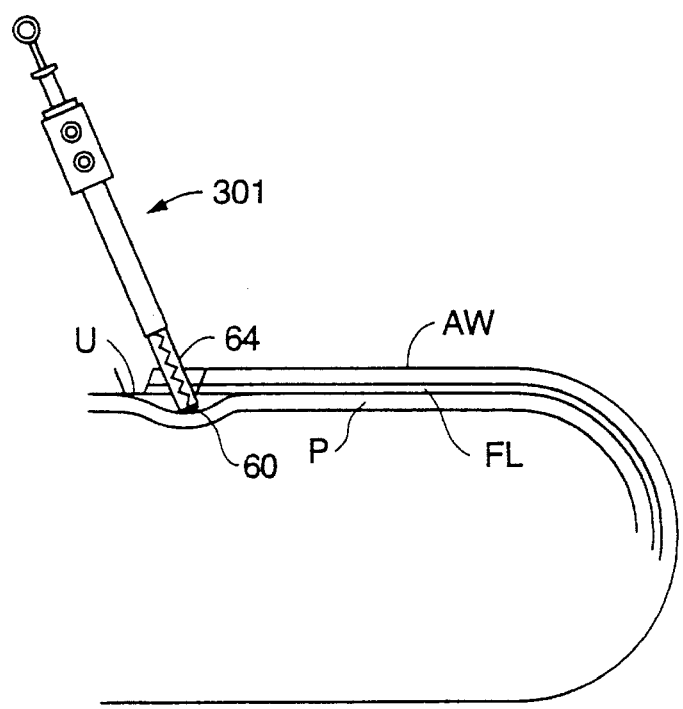
Figure 10C:
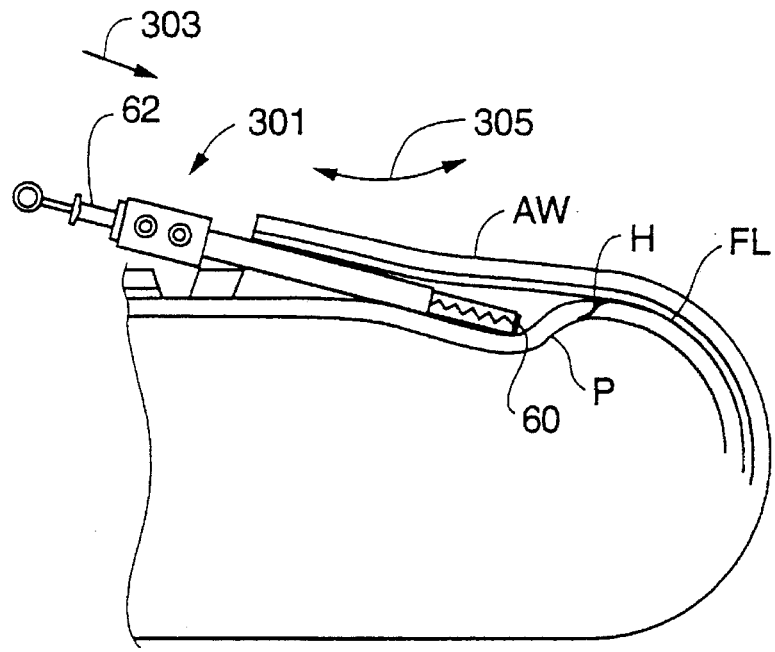

The distal tip of the package is then gently advanced slightly further to nudge the peritoneum P away from the properitoneal fat layer FL in the immediate vicinity of the incision I, as shown in FIG. 10B. The insertion shaft 62 extending the length of the packaged inflatable retraction device 301 to the button 60 in the center of the removable window 18 (not shown) makes the packaged inflatable retraction device rigid, and enables the packaged inflatable retraction device to be used as a blunt dissection tool to dissect to pefitoneum away from the properitoneal fat layer.

The angle between the packaged inflatable retraction device 301 and the abdominal wall AW is then reduced to allow the distal tip of the packaged inflatable retraction device 301 to be advanced between the peritoneum and the properitoneal fat layer FL. The packaged inflatable retraction device is advanced in the direction of the arrow 303, inferiorly towards the site of the hernia H. As the surgeon advances the packaged inflatable retraction device towards the site of the hernia, the packaged inflatable retraction device gently dissects the peritoneum away from the properitoneal fat layer. The surgeon may also sweep the packaged inflatable retraction device laterally in the direction shown by the arrow 305 to widen the area in which the peritoneum is dissected.

Figure 10D:
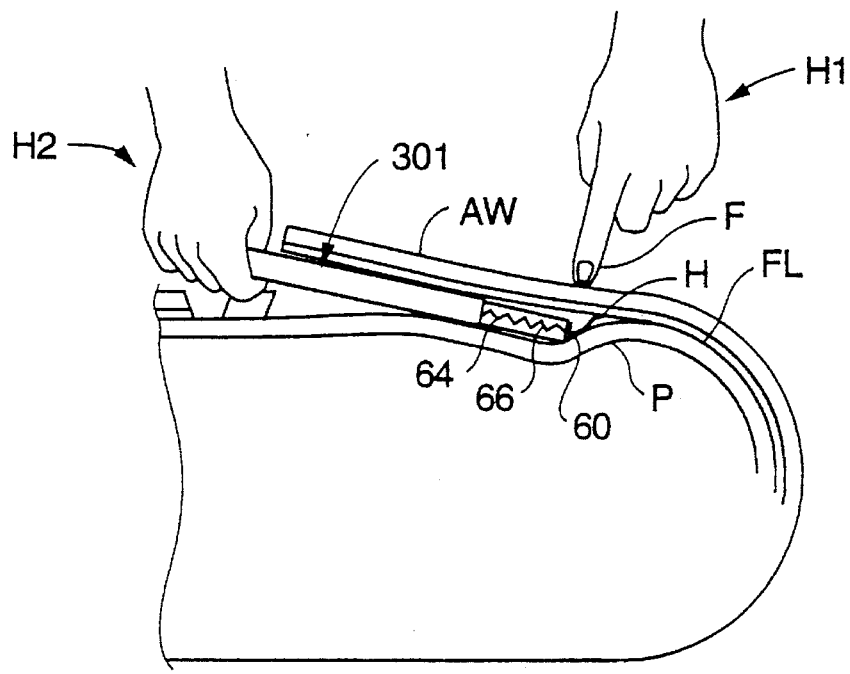

The surgeon may center the removable window 18 (FIG. 1A) of the inflatable retraction device 10 on the site of the hernia H by feel. To do this, the surgeon first locates the site of the hernia H by feel, using the finger F of her hand H1. The surgeon leaves her finger at the site of the hernia, and, using her other hand H2, advances the packaged inflatable retraction device 301 towards her finger located at the site of the hernia. The surgeon stops advancing the packaged inflatable retraction device when she can feel the distal end 60 of the packaged inflatable retraction device with her finger F located at the site of the hernia, as shown in FIG. 10D.

Alternatively, if the button 60 has a center with a known optical characteristic, an endoscope can be inserted into the insertion shaft 62, as shown in FIG. 9C, to allow the position of the button 60 (and hence of the center of the removable window 18) relative to the site of the hernia to be determined by observation using the endoscope.

Once the button 60 is centered on the site of the hernia H, the detachable lacing 66 is removed, which releases the removable sheath 64 from the packaged inflatable retraction device. The removable sheath is removed from the incision I by pulling on the detachable lacing at the end of the procedure.

Figure 10E:
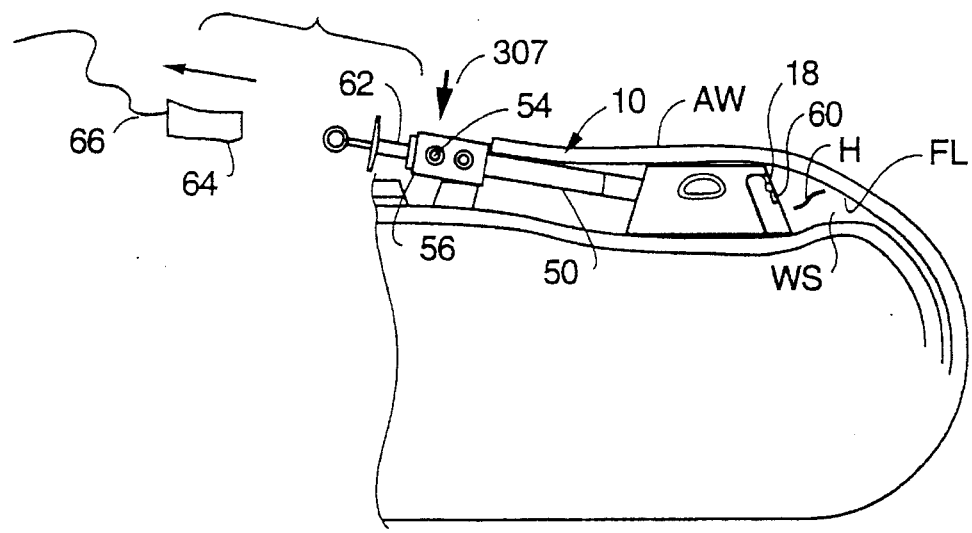
Figure 10F:
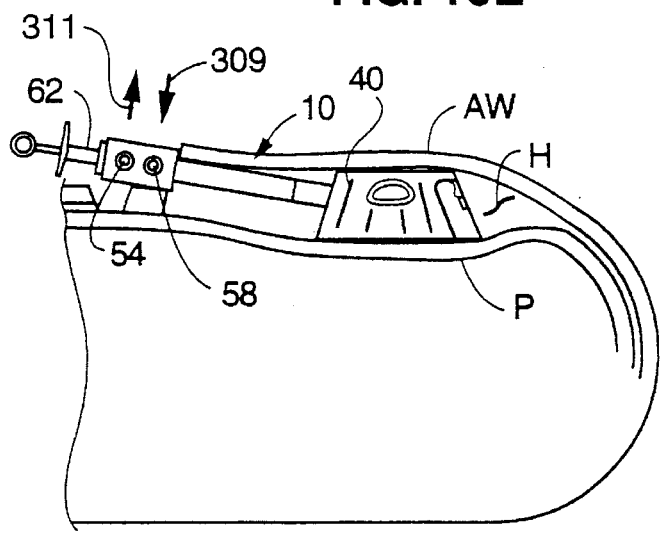

A source of inflation fluid (not shown) is applied to the pressure control valve 54 on the insertion port 56 on the inflation tube 50. The inflation fluid, which is preferably compressed air or carbon dioxide, flows into the pressure control valve 54, as indicated schematically by the arrow 307, and expands the main chamber of the inflatable retraction device 10 to its expanded state. As the main chamber expands, it gently dissects more of the pefitoneum P away from the properitoneal fat layer FL, as shown in FIG. 10E, creating a large working space WS around the site of the hernia H. During the expansion process, the insertion shaft 62 keeps the removable window 18 centered on the site of the hernia H, so that when the expansion process is complete, the site of the hernia is centered in the removable window.

After the main chamber of the inflatable retraction device has reached its fully-expanded state, the source of inflation fluid (not shown) is detached from the pressure control valve 54 on the port 56, and is transferred to the one-way valve 58 on the port 56. The source of inflation fluid is turned on to expand the second chamber of the inflatable retraction device 10. Inflation fluid flows through the one-way valve into the second chamber, as indicated schematically by the arrow 309, shown in FIG. 10F. While the second chamber is expanding, the pressure control valve 54 bleeds off excess inflation fluid from the main chamber to maintain the pressure in the main chamber below the level that could impair the reliability of the main chamber, as indicated schematically by the arrow 311. The baffles, such as the baffle 40, in the now-expanded second chamber are now visible in FIG. 10F.

Figure 10G:
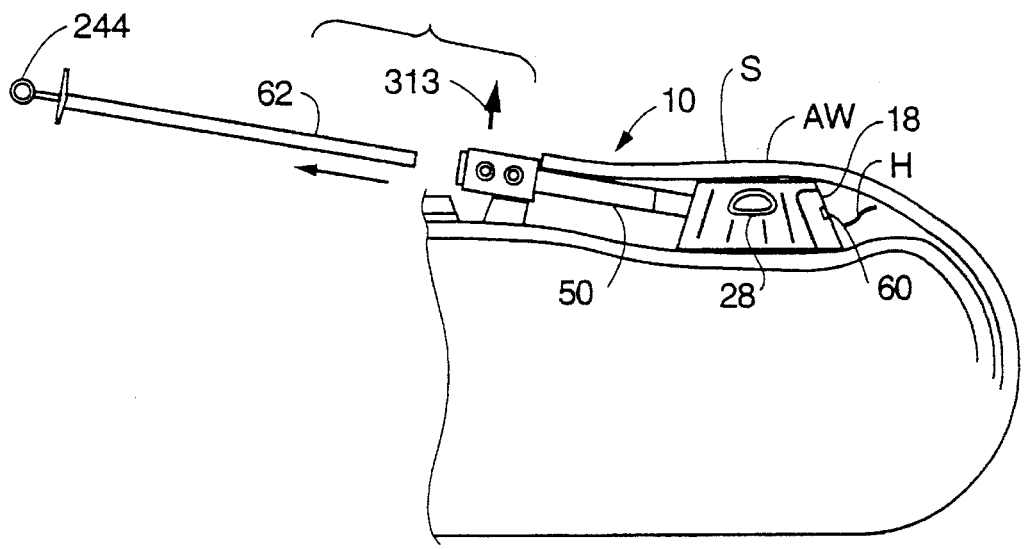

When the second chamber is fully expanded, the inflation pressure in the main chamber is released, as indicated schematically by the arrow 313 in FIG. 10G. The second chamber in its expanded state maintains the retraction originally provided by the main chamber. The surgeon then operates the release button 244 on the insertion shaft 62 to detach the insertion shaft from the button 60. The surgeon then removes the insertion shaft from the inflation robe 50. An endoscope (not shown) is inserted into the inflation tube to cotfin the orientation of the removable window 18 relative to the site of the hernia H.

Figure 10H:
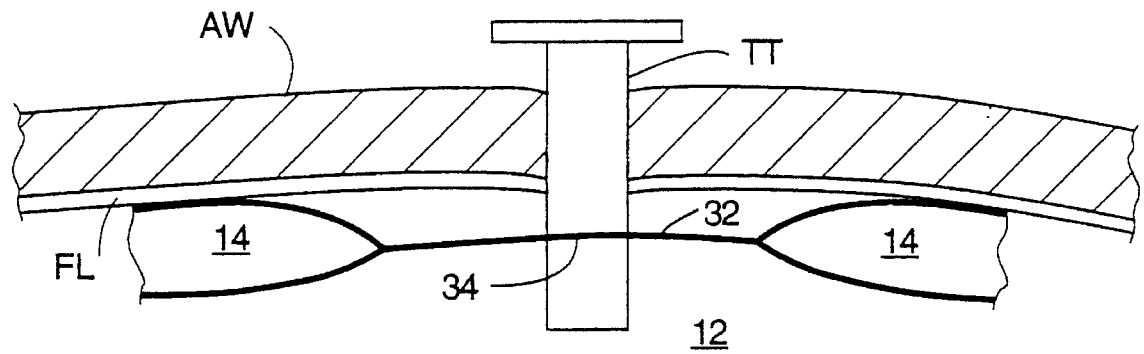
Figure 10:
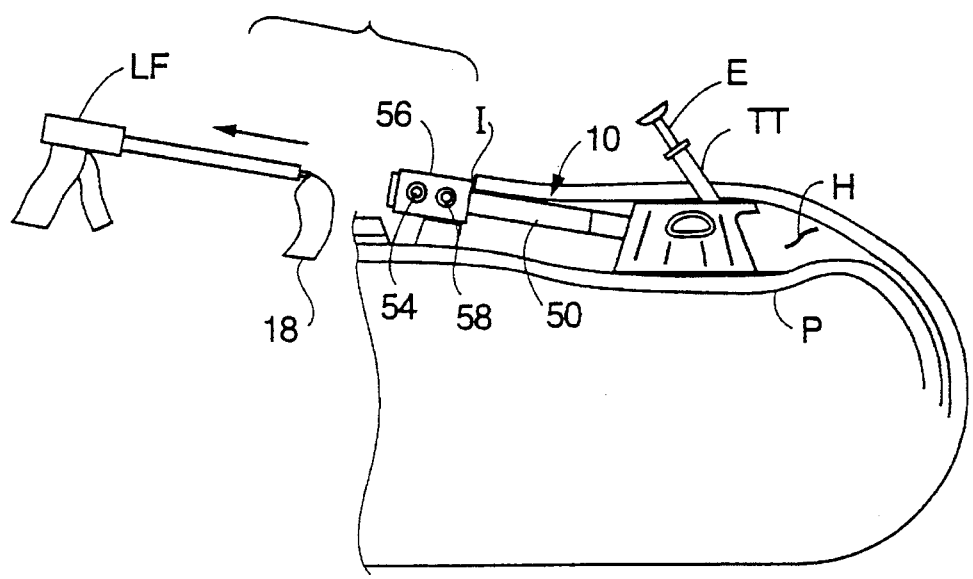

The endoscope is then reorientated to observe the top wall window 32 of the inflatable retraction device. A probe (not shown) is pressed into the skin S of the abdominal wall AW and is moved around near the location of the top wall window. The protrusion in the properitoneal fat layer caused by pressing the probe into the skin of the abdominal wall can be seen using the endoscope observing through the top wall window. The probe is moved until the provision is centered in the top wall window. The trocar (not shown) in the trocar tube TT is placed at the location of the probe, and is driven through the abdominal wall and through the top-wall window 32 to pierce the aperture 34 into the inflatable retraction device, as shown in FIG. 10H. The distal end of the trocar projects in to the main chamber.

Additionally or alternatively, the technique just described may be used to drive a trocar through the abdominal wall to the side of the inflatable retraction device, and through the side window 28 in the inflatable retraction device to pierce an aperture therein.

The trocar is removed, leaving the trocar tube TT in place. The endoscope E is transferred to the trocar tube, as shown in FIG. 10I. Laparoscopic forceps LF are then inserted through the port 56 into the inflation tube 50 to engage the tab on the removable window 18. The laparoscopic forceps are then used to gently peel the removable window away from the side wall of the main chamber and to remove the detached window material from the main chamber, as shown in FIG. 10I. Alternatively, the detached window material can be left in the main chamber. Removing the inflatable retraction device at the end of the procedure will then automatically remove the window material from the body. As a further alternative, detaching the removable window may result in the window material being only partially detached from the main envelope. The detached window material is then pulled out of the way to provide access to treat the hernia.

Figure 10J:
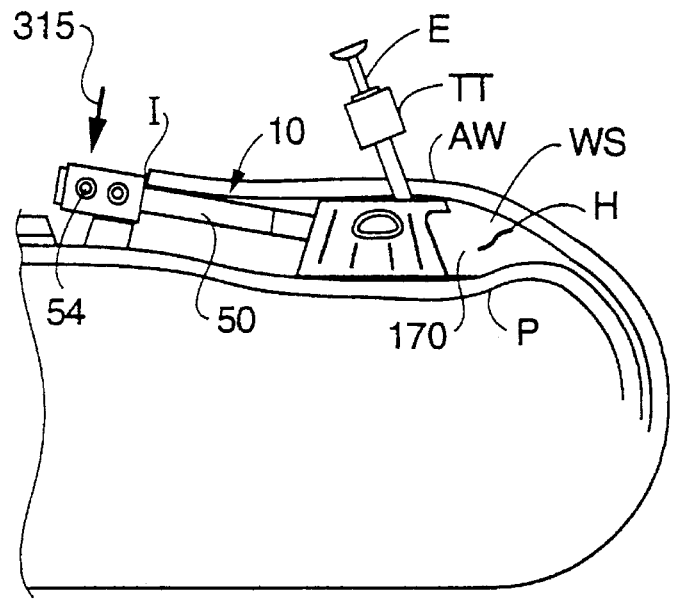

Because of the large area of the removable window 18, it is desirable to supplement the retraction force provided by the second inflatable chamber of the inflatable retraction device 10 by insufflating the working space WS. The inflation tube 50 includes a sealing flange (not shown) that forms a gas-tight seal with the incision I. In addition, a gas-tight trocar tube is used for the trocar tube TT, as shown in FIG. 10J. Insufflation gas is passed into the pressure control valve 54 on the port 56, as indicated schematically by the arrow 315. The insufflation gas passes through the bore of the inflation tube 50 into the main chamber, and out into the working space WS through the aperture 170 left by removing the removable window.

Figure 10K:
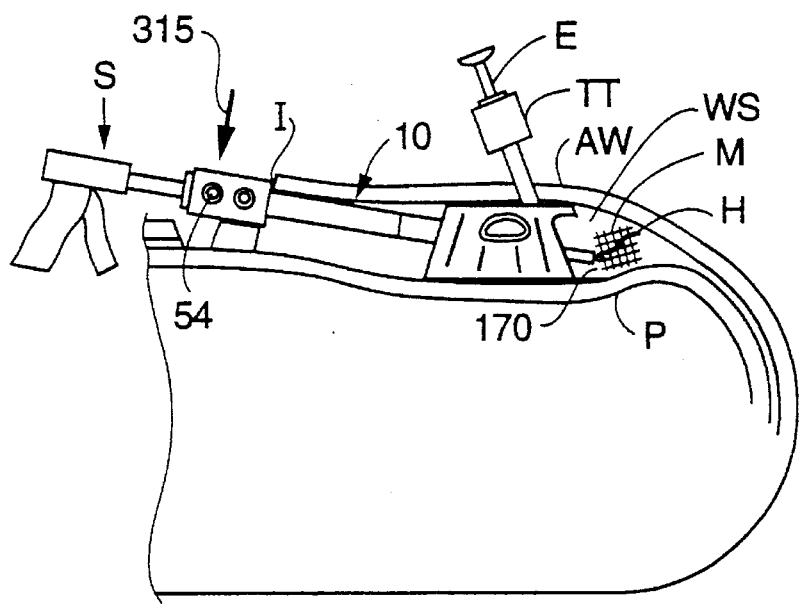

The aperture 170 left by removing the removable window provides access to repair the hernia using instruments and supplies passed through the inflation tube 50 and the trocar tube TT. For example, FIG. 10K shows the laparoscopic stapler S stapling the mesh M over the site of the hernia H.

After the hernia repair procedure is complete, instruments are withdrawn from the main chamber, and the inflatable retraction device is collapsed by evacuating the second chamber. The collapsed inflatable retraction device is then withdrawn from the incision I, and the incision I and the trocar puncture are sutured to complete the procedure.

In the method according to the invention just described, the embodiment of the inflatable retraction device shown in FIGS. 1A through 1E is left in place to maintain the working space while the hernia is being treated, and the hernia is treated working through the inflatable retraction device. The method according to the invention has a number of advantages over a properitoneal hernia repair procedure in which a single-chamber inflatable retraction device is used to dissect the peritoneum from the properitoneal layer to create the working space, is then withdrawn from the working space, and separation of the peritoneum from the properitoneal fat layer is maintained by insufflation of the working space alone. First, no insufflation, or a lower insufflation pressure, may be used in the method according to the invention. Second, even if insufflation is used, and the peritoneum is breached during the blunt dissection process, and insufflation gas enters the abdomen, resulting in a reduced pressure differential across the peritoneum, the inflatable retraction device keeps the peritoneum out of the working space, and prevents the peritoneum from rising up and obstructing access to the site of the hernia. Finally, the inflation robe 50 (or the trocar tube TT entering the main chamber through the top- or side-wall window) provides a clean and direct access route to the site of the hernia for the endoscope. On its way to the site of the hernia, the endoscope does not contact tissue that could deposit blood on the lens of the endoscope.

The method just described can be adapted to other procedures involving blunt dissection. Such procedures include nephrectomy, adrenalectomy, spine surgery, including dissection and spinal fixation, and pericardiectomy.

9. Intra-Abdominal Procedure

Figure 11A:
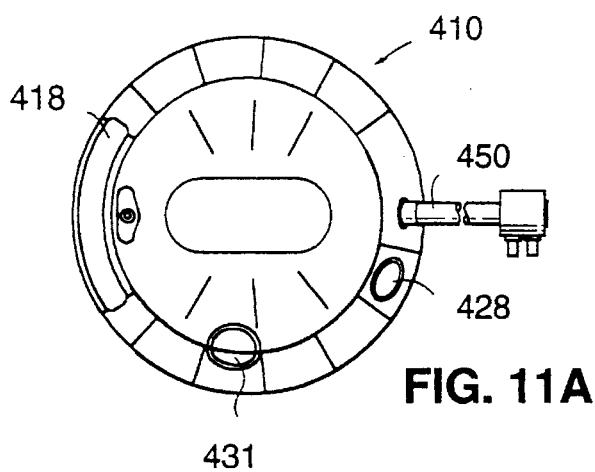
FIG. 11A shows an embodiment of the inflatable retraction device according to the invention for use for retracting organs in the abdomen.

An intra-abdominal procedure according to the invention will now be described. As an example, a method of using an inflatable retraction device according to the invention to lift the liver to gain access to treat the gall bladder will now be described. In the method, an inflatable retraction device 401 shown in FIG. 11A is used. The inflatable retraction device is similar to that shown in FIG. 7A. However, the removable window 418 is on the center line defined by the inflation tube 450, and the device is about 50% larger (about 9"–10' (225–250 mm) in diameter). Additionally, the side-wall window 428 is located about 30 degrees to the left of the midline, and an additional window 431 is provided at about 90 degrees to the left of the midline. The additional window spans the side wall and the top wall of the main chamber. These windows are optimally located for the gall bladder procedure.

The inflatable retraction device 401 is preferably packaged as shown in FIG. 9A. The packaged inflatable retraction device is indicated by the reference numeral 402.

Although the gall bladder treatment method does not involve carrying out blunt dissection, the packaged inflatable retraction device nevertheless includes the insertion shaft 462, which is used to help position the inflatable retraction device before it is expanded. The insertion shaft also serves to control the location of the removable window (not shown) during the expansion process. Finally, a small endoscope can be inserted into the insertion shaft, as shown in FIG. 9C, so that the position of the center of the removable window can be checked by direct observation. Alternatively, the packaging shown in FIG. 9E may be used.

Figure 11B:
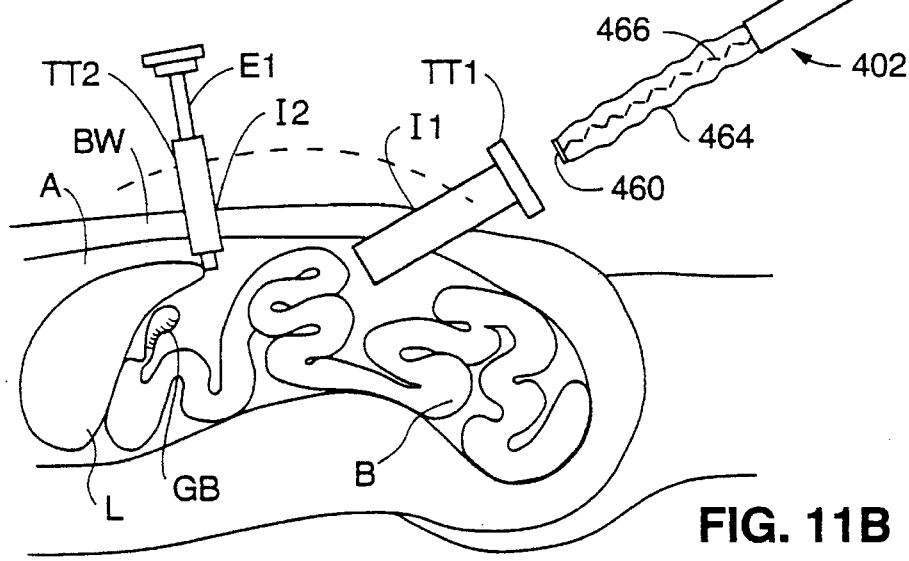
FIGS. 11B through 11G illustrate using the inflatable retraction device according to the invention in the retraction method according to the invention.

Prior to making the first incision, the abdominal wall AW may be lifted to provide additional working space by gas insufflation, or by one of the mechanical devices disclosed in U.S. patent application Ser. No. 07/706,781, of which application the parent of this application is a Continuation-in-Part, or by some other suitable mechanical retraction device. The insufflated state of the abdominal wall AW is indicated in FIG. 11B by the broken line A'.

A small incision I1 is made in the skin of the abdominal wall AW and a trocar (not shown) and trocar tube TT1 are inserted into the incision and are driven through the abdominal wall. The trocar is withdrawn. A second small incision I2 is made in the skin of the abdominal wall AW and a trocar (not shown) and the trocar tube TT2 are inserted into the incision and driven through the abdominal wall. The trocar is withdrawn and the endoscope E1 is inserted into the trocar tube TT2. The second incision I2 is located so that the endoscope E1 can observe the intended placement site of the packaged inflatable retraction device 402, as shown in FIG. 11B. Alternatively, if the small endoscope (not shown) is inserted into the insertion shaft 462 to determine by direct observation the location in the abdomen of the removable window, the endoscope E1 is not used, and the second incision I2 need not be made.

Figure 11C:
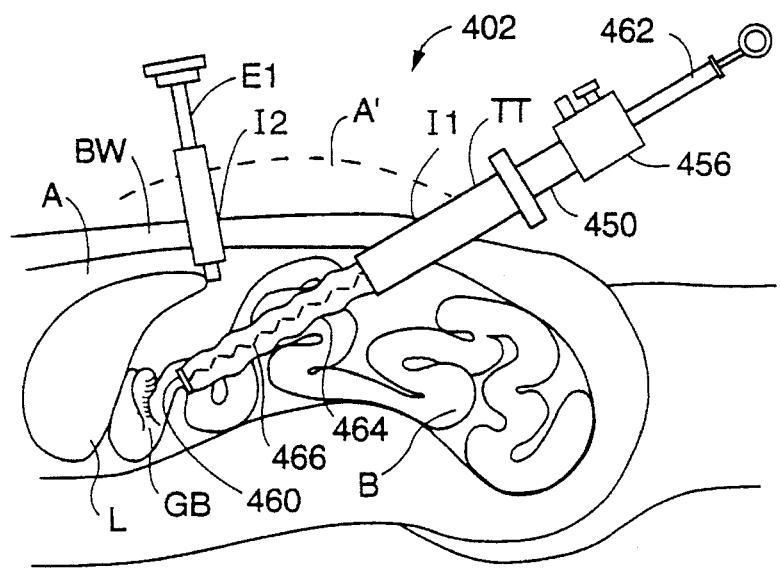

The packaged retraction device 402 is handled by the inflation tube 450 and the insertion shaft 462 and is inserted through the trocar tube TT1 into the abdominal cavity AC, as shown in FIG. 11C, and manipulated into position such that the button 460 in the center of the removable window is adjacent to the position of the gall bladder GB. The position of packaged inflatable retraction device 402 in the abdominal cavity AC is observed through the endoscope E1 and/or the endoscope (not shown) passed through the insertion shaft.

The extension of the removable lacing 466 is then pulled to release the detachable sleeve 464 from around the collapsed inflatable retraction device 402. At the end of the procedure, after the inflatable retraction device 401 has been withdrawn from the trocar tube TT1, the detachable sleeve 464 is withdrawn from the abdominal cavity AC through the trocar tube TT1 by pulling on the removable lacing 466.

Figure 11D:
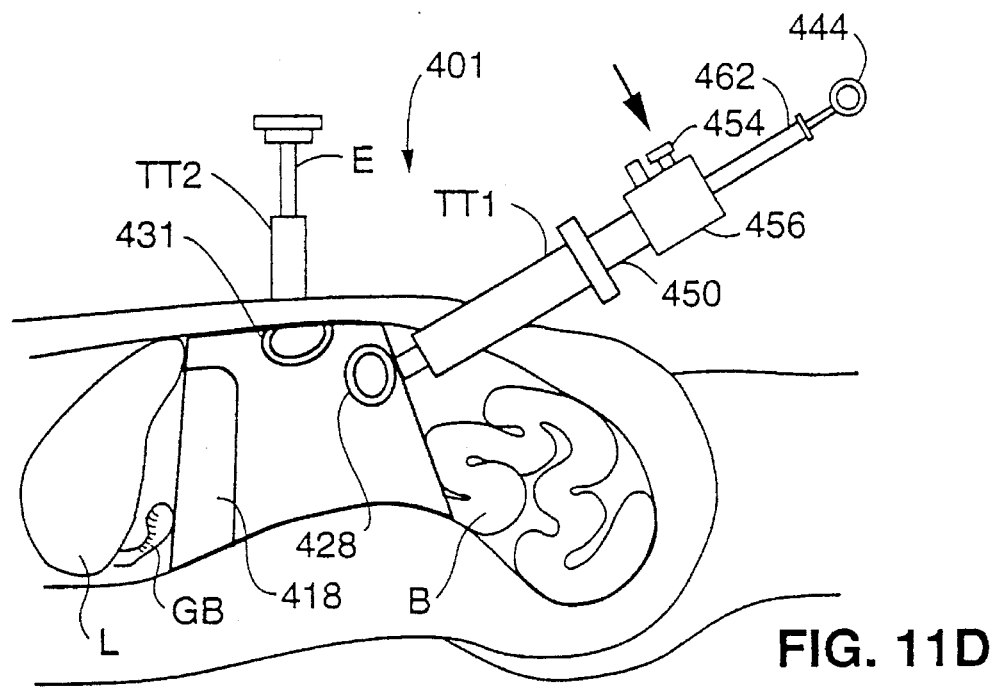

Once the inflatable retraction device 401 is correctly positioned and released from the detachable sleeve 464, the pressure control valve 454 on the port 456 is connected to a source of inflation fluid (not shown) and the fluid supply is slowly turned on to expand the main inflatable chamber of the inflatable retraction device 410. The inflatable retraction device 401 slowly expands, as shown in FIG. 11D, progressively lifting the liver L as its size increases.

When the inflatable retraction device 401 has reached its fully-expanded state, the position of the removable window 418 relative to the gall bladder GB, now exposed by lifting the liver L, is checked by viewing it through the endoscope E1 and/or an endoscope (not shown) inserted into the main chamber 412 via the inflation tube 450 and the port 56, or inserted into the insertion shaft 462. Preferably, the gall bladder should be centered in the removable window 418.

If the inflatable retraction device 401 is not correctly positioned, some inflation fluid may be bled off from the main chamber, and the insertion shaft 462 is used to manipulate the partially-inflated inflatable retraction device 401 to correct the positioning error while the position of the removable window 418 relative to the gall bladder GB is observed through the endoscope E1 or the endoscope (not shown) in the insertion shaft 462. After the positioning error is corrected, the main chamber is reexpanded.

Figure 11E:
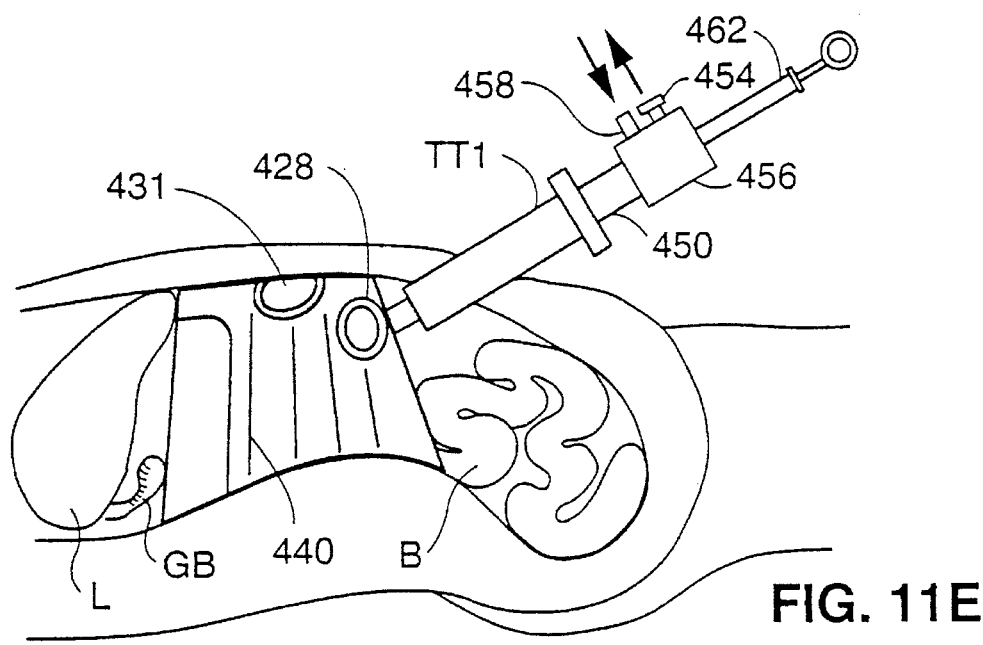

When the inflatable retraction device 401 is correctly positioned, the one-way valve 458 is connected to the source of inflation fluid (not shown) and the second chamber of the inflatable retraction device is expanded, as shown in FIG. 11E. During expansion of the second chamber, the pressure control valve 454 bleeds off excess inflation fluid from the main chamber to maintain the pressure in the main chamber below the level that could impair the reliability of the main chamber. In FIG. 11E, the baffles, such as the baffle 440, can be seen when the second chamber is in its expanded state.

When the second chamber is fully expanded, the inflation pressure in the main chamber 412 can be released. The second chamber in its expanded state maintains the retraction originally provided by the main chamber. The surgeon operates the release button 444 on the insertion shaft 462 to detach the insertion shaft from the button 460. The insertion shaft is then removed from the inflation tube 450. An endoscope is inserted into the inflation tube to confirm the orientation of the removable window 418 relative to the gall bladder.

Figure 11F:
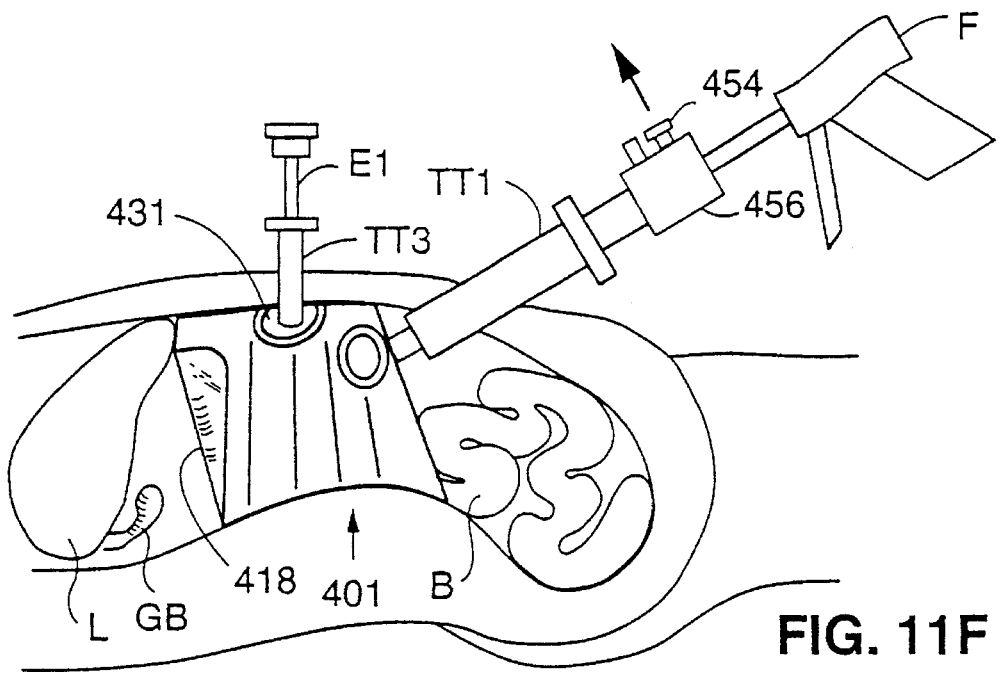

Using the probing technique described above, trocars are centered on the side-wall window 428 and the side-top-wall window 43 1, and are driven into the main chamber through the abdominal wall AW and the respective window. The trocar is removed, leaving the trocar tube TT3 in place, as shown in FIG. 11F. The endoscope E1 is transferred to the trocar tube. Laparoscopic forceps F are then inserted into the inflation tube to engage the tab on the removable window 418. The laparoscopic forceps are then used to gently peel the removable window away from the side wall of the main chamber, as shown in FIG. 11F, and to remove the detached window material from the main chamber. Alternatively, the detached window material can be left in the main chamber. Removing the inflatable retraction device at the end of the procedure will then automatically remove the window material from the body. As a further alternative, detaching the removable window may result in the window material being only partially detached from the main envelope. The detached window material is then pulled out of the way to provide access to treat the hernia.

Figure 11G:
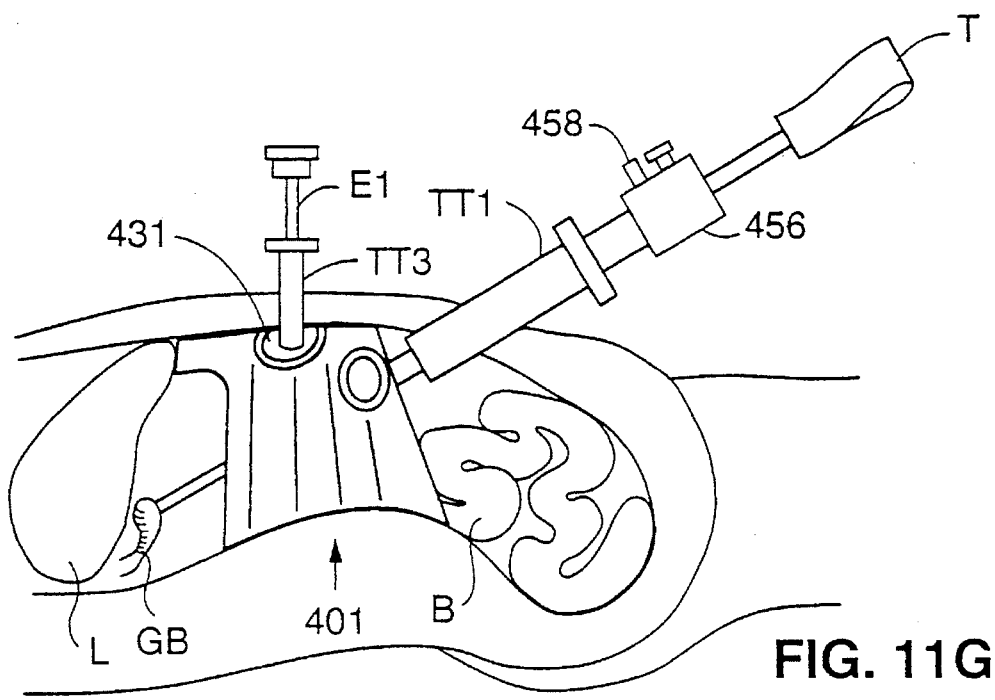

The aperture left by removing the removable window provides access to treat the gall bladder using instruments and supplies passed through the inflation tube 450 and the trocar tube TT3. FIG. 11G shows the gall bladder tool T in the process of draining bile from the gall bladder GB in preparation to remove the gall bladder GB.

After the treatment is completed, the inflation pressure in the second chamber 414 is released to collapse the inflatable retraction device. Collapsing the retraction device is assisted by connecting the one-way valve 458 to a vacuum line (not shown) to evacuate the second chamber. When the inflatable retraction device 401 is fully collapsed, the trocar tube TT2 is withdrawn from the abdominal cavity, the retraction device 10 is withdrawn through the small incision, and the incisions in the abdominal wall are sutured in the normal way.

In addition to the procedures described above, the inflatable retraction device and methods according to the invention may be used in such procedures as bladder neck suspension procedures, lymphadenectomy, varicocelemitomy, appendectomy, reflux surgery, such as Nissen fundoplication, vagotomy, vascular surgery, splenectomy, colectomy, gastrectomy and gastronomy, esophageal myotomy, e.g., Heller myotomy, lung surgery, such as resection of lung tissue, and lobectomy, pericardiectomy, and other cardiac surgery.

Although this application describes illustrative embodiments of the invention in detail, it is to be understood that the invention-is not limited to the precise embodiments described, and that various modifications may be practiced within the scope of the invention defined by the appended claims.

We claim:

1. A method for properitoneal hernia repair, the method comprising the steps of:

providing an inflatable retraction device in a compacted state, the inflatable retraction device including:

a main envelope enclosing a main chamber, the main envelope including a window and a removable window, a second envelope covering substantially all the main envelope, except the window and the removable window, the second envelope and the main envelope enclosing a second chamber outside the main chamber, an attachment point centered in the removable window, and an insertion shaft passing through the main chamber, and having a distal end temporarily attached to the attachment point, the attachment point providing a distal tip for the inflatable retraction device;

making an incision through the abdominal wall at the umbilicus as far as the properitoneal layer;

inserting the distal tip of the inflatable retraction device into the incision;

using the inflatable retraction device to dissect the peritoneum from the properitoneal layer while advancing the inflatable retraction device inferiorly between the peritoneum and the properitoneal layer towards the hernia;

passing a fluid into the main chamber to expand the main chamber and the second chamber from the compacted state to dissect further the peritoneum from the properitoneal layer;

passing a fluid into the second chamber to further expand the second chamber;

releasing fluid from the main chamber; and detaching the removable window from the main envelope.

2. The method of claim 1 additionally comprising the step of repairing the hernia using an instrument passed through the main chamber.

3. The method of claim 1, additionally comprising the step of detaching the insertion shaft from the removable window before the step of detaching the removable window.

4. The method of claim 1, wherein:

the step of passing a fluid into the main chamber expands the main chamber to create a working space; and after the step of detaching the removable window, the method additionally comprises the step of passing insufflation gas through the main chamber to insufflate the working space.

5. The method of claim 1, additionally comprising the step of driving a trocax through the window into the main chamber.

6. The method of claim 5, wherein the step of driving a trocar through the window includes the steps of:

pressing a probe on the abdominal wall above the window to cause a protrusion in the properitoneal layer;

observing the provision in the properitoneal layer through the window from inside the main chamber;

moving the probe until the provision is centered in the window; and substituting the trocar for the probe.

7. The method of claim 1, wherein the step of using the inflatable retraction device to dissect the pefitoneum from the properitoneal layer is continued until the removable window is centered on the hernia, using the endoscope.

8. The method of claim 1, wherein:

the step of providing a compacted inflatable retraction device provides an insertion shaft having an endoscope mounted therein, the endoscope providing observation through the distal tip of the inflatable retraction device; and the step of using the inflatable retraction device to dissect the peritoneum from the properitoneal layer is continued until the hernia is seen using the endoscope.

9. The method of claim 1, wherein the step of using the inflatable retraction device to dissect the peritoneum from the properitoneal layer includes the steps of:

locating the hernia by feel through the abdominal wall; and advancing the inflatable retraction device until the distal tip of the inflatable retraction device and the hernia are felt together through the abdominal wall.

10. A method for retracting an organ to gain access to treat a tissue, the method comprising the steps of:

providing an inflatable retraction device in a compacted state, the inflatable retraction device including:

a main envelope enclosing a main chamber, the main envelope including a window and a removable window, and a second envelope covering substantially all the main envelope, except the window and the removable window, the second envelope and the main envelope enclosing a second chamber outside the main chamber;

placing the inflatable retraction device in the compacted state adjacent the organ;

passing a fluid into the main chamber to expand the main chamber and the second chamber from the compacted state to retract the organ;

passing a fluid into the second chamber to further expand the second chamber;

releasing fluid from the main chamber; and detaching the removable window from the main envelope.

11. The method of claim 10, additionally comprising the step of treating the tissue using an instrument passed through the main chamber.

12. The method of claim 10, additionally comprising the step of driving a trocar through the window into the main chamber.

13. The method of claim 12, wherein:

the inflatable retraction device is located inside a body wall; and the step of driving a trocar through the window includes the steps of:

pressing a probe onto the body wall above the window to cause a provision in the body wall;

observing the provision in the body wall through the window from inside the main chamber;

moving the probe until the provision is centered in the window; and substituting the trocar for the probe.

14. The method of claim 10, wherein, in the step of placing the inflatable retraction device adjacent the organ, the inflatable retraction device is placed adjacent the organ using an insertion shaft.

15. The method of claim 14, additionally comprising the step of detaching the insertion shaft from the removable window before the step of detaching the removable window.

16. The method of claim 10, wherein:

the step of providing a compacted inflatable retraction device provides an insertion shaft having an endoscope mounted therein, the endoscope providing observation through the distal tip of the inflatable retraction device; and in the step of placing the inflatable retraction device adjacent the organ, the insertion shaft is manipulated until the organ is seen using the endoscope.

* * * * *